US009726622B2

(12) United States Patent
Momose

(10) Patent No.: US 9,726,622 B2
(45) Date of Patent: Aug. 8, 2017

(54) NON-DESTRUCTIVE INSPECTION DEVICE

(71) Applicant: Tohoku University, Sendai-shi, Miyagi (JP)

(72) Inventor: Atsushi Momose, Sendai (JP)

(73) Assignee: Tohoku University, Sendai-shi, Miyagi (JP)

( * ) Notice: Subject to any disclaimer, the term of this patent is extended or adjusted under 35 U.S.C. 154(b) by 0 days.

(21) Appl. No.: 15/033,440

(22) PCT Filed: Oct. 30, 2014

(86) PCT No.: PCT/JP2014/078994
§ 371 (c)(1),
(2) Date: Apr. 29, 2016

(87) PCT Pub. No.: WO2015/064723
PCT Pub. Date: May 7, 2015

(65) Prior Publication Data
US 2016/0252470 A1 Sep. 1, 2016

(30) Foreign Application Priority Data
Oct. 31, 2013 (JP) .................... 2013-226437
Apr. 17, 2014 (JP) .................... 2014-085843

(51) Int. Cl.
*G01N 23/201* (2006.01)
*G01N 23/20* (2006.01)
(Continued)

(52) U.S. Cl.
CPC ..... *G01N 23/20075* (2013.01); *A61B 6/4035* (2013.01); *A61B 6/4291* (2013.01);
(Continued)

(58) Field of Classification Search
CPC .. G01N 23/20075; A61B 6/484; A61B 6/502; A61B 6/032; A61B 6/06; A61B 6/505;
(Continued)

(56) References Cited

U.S. PATENT DOCUMENTS 5,812,629 A 9/1998 Clauser
7,180,979 B2 2/2007 Momose
(Continued)

FOREIGN PATENT DOCUMENTS

JP 2008-145111 A 6/2008
JP 2008-545981 A 12/2008
(Continued)

OTHER PUBLICATIONS

International Search Report, mailed Feb. 17, 2015, for corresponding International Application No. PCT/JP2014/078994, 2 pages.
(Continued)

*Primary Examiner* — Irakli Kiknadze
(74) *Attorney, Agent, or Firm* — Seep IP Law Group LLP

(57) ABSTRACT

An accurate non-destructive inspection of a moving subject is conducted using a radiation source unit that irradiates radioactive rays toward gratings. Each grating includes a plurality of grating members. A radioactive ray detector unit detects the radioactive rays diffracted by the plurality of grating members. The plurality of grating members are arranged with a predetermined phase difference such that moiré pattern images respectively formed by the radioactive rays transmitted through first to third partial areas have a phase difference between the moiré pattern images.

14 Claims, 28 Drawing Sheets

(51) Int. Cl.
*A61B 6/00* (2006.01)
*G21K 1/06* (2006.01)

(52) U.S. Cl.
CPC .............. *A61B 6/484* (2013.01); *G21K 1/06* (2013.01); *G21K 2207/005* (2013.01)

(58) Field of Classification Search
CPC ......... A61B 6/482; A61B 6/504; A61B 6/508; A61B 6/00; A61B 6/485; A61B 6/14; A61B 6/50; A61B 6/503; A61B 6/04; A61B 6/48; A61B 6/583; A61B 6/58; A61B 6/4291; A61B 6/4035; A61B 6/5205; A61B 6/4233; A61B 6/4441; A61B 6/5258; A61B 6/4007; A61B 6/4241; A61B 6/4458; A61B 6/5217; A61B 6/587; A61B 6/4092; A61B 6/4021; A61B 6/5235; A61B 6/4464; A61B 6/4488; A61B 6/5282; A61B 2503/04
USPC ..................... 378/36, 37, 62; 382/128–132
See application file for complete search history.

(56) References Cited

U.S. PATENT DOCUMENTS

| | | | | |
|---|---|---|---|---|
| 8,041,004 | B2* | 10/2011 | David | A61B 6/484 378/36 |
| 2005/0286680 | A1* | 12/2005 | Momose | A61B 6/06 378/62 |
| 2007/0183583 | A1* | 8/2007 | Baumann | A61B 6/032 378/145 |
| 2009/0092227 | A1 | 4/2009 | David et al. | |
| 2010/0061508 | A1* | 3/2010 | Takahashi | A61B 6/00 378/36 |
| 2010/0074395 | A1 | 3/2010 | Popescu | |
| 2011/0200168 | A1* | 8/2011 | Ouchi | G01N 23/04 378/36 |
| 2011/0235775 | A1* | 9/2011 | Tada | A61B 6/00 378/36 |
| 2012/0189101 | A1 | 7/2012 | Kaneko | |
| 2012/0288056 | A1 | 11/2012 | Murakoshi et al. | |
| 2014/0112440 | A1 | 4/2014 | David et al. | |

FOREIGN PATENT DOCUMENTS

| | | |
|---|---|---|
| JP | 2009-240378 A | 10/2009 |
| JP | 2012-085995 A | 5/2012 |
| JP | 2013-529984 A | 7/2013 |
| WO | 2004/058070 A1 | 7/2004 |
| WO | 2012/029005 A1 | 3/2012 |
| WO | 2013/111050 A1 | 8/2013 |

OTHER PUBLICATIONS

Momose et al., "Demonstration of X-Ray Talbot Interferometry," *Japanese Journal of Applied Physics* 42:L866-L868, Jul. 15, 2003.
Momose et al., "High-speed X-ray phase imaging and X-ray phase tomography with Talbot interferometer and white synchrotron radiation," *Optics Express* 17(15): 12540-12545, Jul. 20, 2009.
Momose, "X-ray phase imaging based on Talbot effect," *Japanese Society for Synchrotron Radiation Research* 23(6):382-392, Nov. 2010. (Article in Japanese).
Pfeiffer et al., "Phase retrieval and differential phase-contrast imaging with low-brilliance X-ray sources," *Nature Physics* 2:258-261, Apr. 2006.
Takeda et al., "Fourier-transform method of fringe-pattern analysis for computer-based topography and interferometry," *J. Opt. Soc. Am.* 72(1):156-160, Jan. 1982.
Pfeiffer, F. et al., "Neutron Phase Imaging and Tomography", The American Physical Society, 2006, pp. 215505-1-215505-4.
Extended European Search Report for Application No. 14857299.3, dated Nov. 7, 2016, 10 pgs.
Momose, A. et al., "Grating-Based X-ray Phase Imaging Using Multiline X-ray Source", Japanese Journal of Applied Physics 48, 076512, Jul. 1, 2009, 6 pgs.

* cited by examiner

FIG. 6

| | WITHOUT DEVICE CORRECTION | WITH CORRECTION BY DATA MEASURED IN ADVANCE IN ABSENCE OF SAMPLE (SUPERSCRIPT '0') |
|---|---|---|
| OPERATIONAL EXPRESSION FOR ABSORPTION IMAGE | $I_1(x,t)+I_2(x,t+\tau_a)+I_3(x,t+\tau_b)$ | $\dfrac{I_1(x,t)+I_2(x,t+\tau_a)+I_3(x,t+\tau_b)}{I_1^0(x,t)+I_2^0(x,t+\tau_a)+I_3^0(x,t+\tau_b)} \equiv T(x,t)$ |
| OPERATIONAL EXPRESSION FOR REFRACTION IMAGE | $\arg[S(x,t)]$ | $\arg\left[\dfrac{S(x,t)}{S^0(x,t)}\right]$ |
| OPERATION EXPRESSION FOR SCATTERING IMAGE | $\dfrac{2S(x,t)}{I_1(x,t)+I_2(x,t+\tau_a)+I_3(x,t+\tau_b)}$ | $\dfrac{S(x,t)}{S^0(x,t)\,T(x,t)}$ |

WHERE, $S(x,t) \equiv I_1(x,t)+I_2(x,t+\tau_a)\exp\left[\dfrac{2}{3}\pi i\right]+I_3(x,t+\tau_b)\exp\left[\dfrac{4}{3}\pi i\right]$

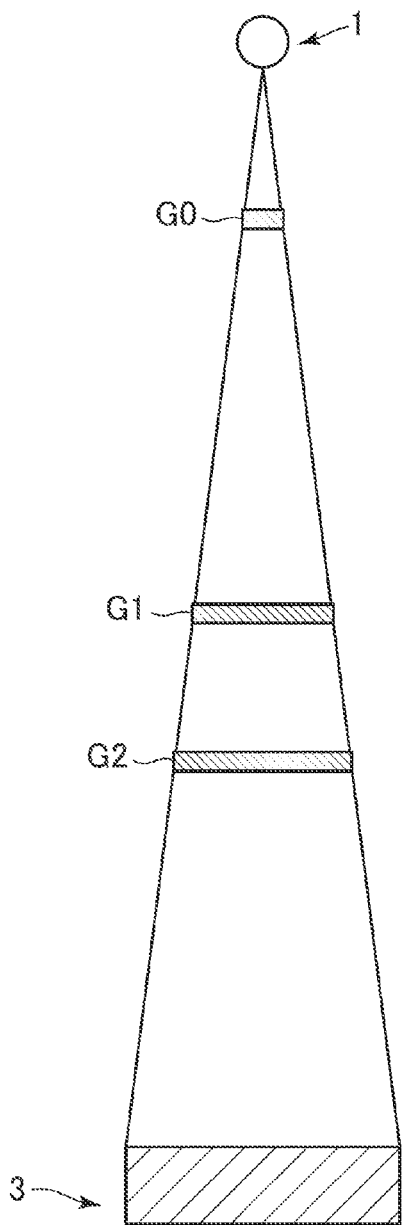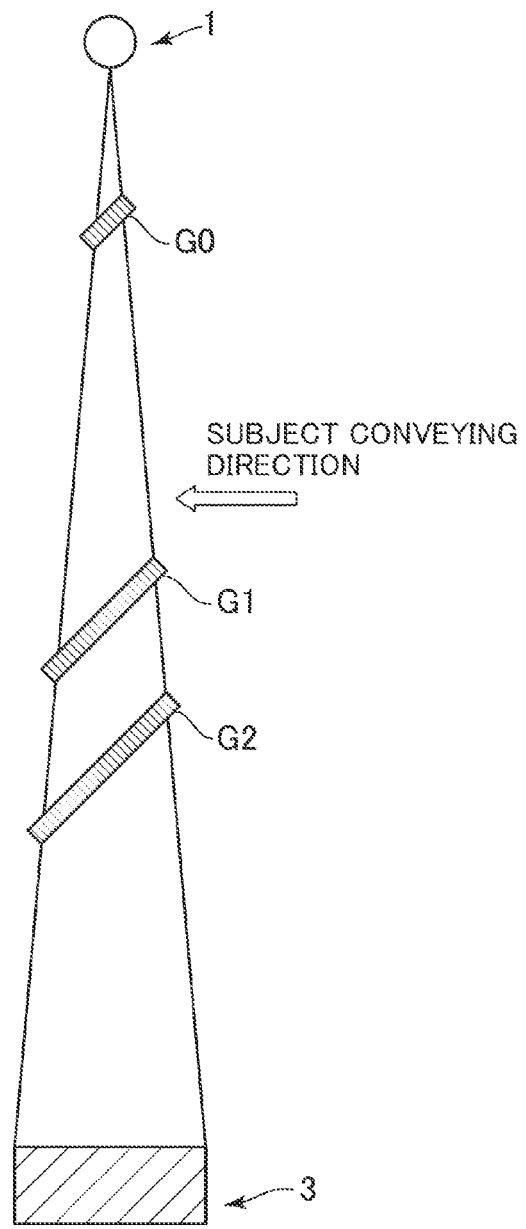

NON-DESTRUCTIVE INSPECTION DEVICE

BACKGROUND

Technical Field

The present disclosure relates to a non-destructive inspection device for observing an internal structure of a subject with high sensitivity utilizing properties as waves of radioactive rays transmitted through the subject, e.g., X-rays.

Description of the Related Art

Radioactive rays having high transmission power such as X-rays are widely used as a probe for seeing through an object's interior in medical image diagnosis, non-destructive inspection, security check and the like. Contrast of an X-ray radiograph differs depending on an X-ray attenuation ratio, and an object which strongly absorbs X-rays is drawn as the shadow of the X-rays. X-ray absorption capability becomes stronger as more elements with large atomic numbers are contained. Conversely, it can be pointed out that an object composed of elements with small atomic numbers has low contrast. This is a principle defect of X-ray radiographs. Thus, sufficient sensitivity cannot be obtained for biological soft tissues and polymers.

On the other hand, if the properties as waves of X-rays are utilized, higher sensitivity potentially about three orders of magnitude larger than general conventional X-ray radiographs can be realized. Hereinafter, this is called an X-ray phase contrast method. If this technique is applied to the observation of an object (biological soft tissue, polymers or the like) composed of light elements which do not absorb X-rays very much, an inspection which has been difficult by conventional methods is enabled. Thus, its practical use is expected.

To realize a high-sensitivity imaging method utilizing the X-ray phase contrast method, X-ray optical systems using monochromatic plane waves of X-rays have been mainly studied so far, wherefore the use of an X-ray source having very high luminance is assumed.

To obtain monochromatic plane waves, only specific spectrum components which propagate in a specific direction need to be selected from originally obtained X-rays. Thus, to ensure intensity necessary for imaging, the original X-rays are required to have brightness sufficient to compensate for loss caused due to the selection. A single crystal such as silicon is used as an optical element for performing such a selection, but the use of a huge synchrotron radiation facility has to be substantially assumed, which is a large obstacle in considering practical use.

If the X-ray phase contrast method that functions with a cone beam having a wide band width is realized, a device using a compact X-ray source other than synchrotron radiation can be expected. An X-ray phase contrast method by an X-ray Talbot interferometer is expected as a candidate of such an imaging method (see patent literature 1 and 2 below). Since not single crystals, but X-ray gratings are used in this method, imaging utilizing polychromatic diverging X-rays is possible.

However, in the phase contrast method, X-rays are required to have a certain degree of spatial coherence. For that, the size of an X-ray generation source has to be reduced to a certain extent. Then, the pre-existing compact X-ray sources usable in this method are substantially micro-focus X-ray sources. Normal-focus X-ray sources are not applicable to this.

In the micro-focus X-ray source, X-rays are generated by irradiating electron beams to a minute area of a target. Many electrons need to be irradiated when it is desired to generate many X-rays. However, due to a problem of thermal load in the target, an upper limit of actual X-ray power is restricted. As a result, if X-ray imaging is performed, assuming the power of X-rays obtained by the micro-focus X-ray source, there is a problem of extending an exposure time.

In a conventional X-ray Tablot-Lau interferometer, a problem of intensity shortage is avoided using a normal-focus X-ray source. The X-ray Tablot-Lau interferometer is so configured that a multi-slit is added between an X-ray source and a G1 grating of an X-ray Talbot interferometer (see patent literature 3, 4 and non-patent literature 1 below). It should be noted that the multi-slit is called a G0 grating in some cases, but this multi-slit is for configuring virtual X-ray sources. Specifically, in this technology, X-rays are generated by irradiating electron beams to a relatively wide area on the target and the generated X-rays are partly transmitted through the multi-slit. In this way, it is possible to realize an X-ray source in which narrow and linear virtual X-ray sources are arranged at predetermined pitches. It should be noted that an X-ray source having a plurality of microlines is called a micro multi-line X-ray source in some cases.

The X-ray Tablot-Lau interferometer can be called a technology realizing the X-ray source in the X-ray Tablot interferometer by the normal-focus X-ray generator and the multi-slit and should be called a specific form of the X-ray Tablot interferometer.

In a phase contrast method by X-ray Tablot interferometers including Tablot-Lau interferometers, a moiré pattern image is recorded by an X-ray detector. In this image, an effect of X-ray refraction by a subject is visualized. However, absorption contrast corresponding to conventional images is also superimposed and contrast unrelated to the subject is also added due to the imperfection of an imaging optical system and a device. To separate these and conduct a more precise and advanced inspection, development towards a quantitative image measurement technology called an "X-ray phase imaging method" has been proposed. To realize the phase imaging method in the X-ray Tablot interferometer, procedures called a "fringe scanning method" (non-patent literature 2) and a "Fourier transform method" (non-patent literature 3 and non-patent literature 4) are carried out. The fringe scanning method is a method for obtaining an absorption image, a refraction image and a scattering image through computer arithmetic processing by moving any one of gratings by a predetermined step amount each time and successively imaging a subject to obtain a change of a moiré pattern in the form of a plurality of pieces of image data. On the other hand, the Fourier transform method is a method for similarly obtaining an absorption image, a refraction image and a scattering image from one moiré fringe image through predetermined Fourier filtering by inclining one grating to generate fine rotational moiré fringes. The Fourier transform method has a problem of being inferior in spatial resolution as compared to the case where the fringe scanning method is applied. Thus, the fringe scanning method is considered to be suitable for detailed inspection of the subject. It should be noted that the absorption image corresponds to a conventional image, the refraction image is an image mapping deflection angles of X-rays by refraction in the subject and the scattering image is an image mapping a reduction in the visibility of the moiré pattern by the subject. Since this visibility reduction corresponds to a distribution of fine scatterers included in the subject, this is called the scattering image.

In the fringe scanning method, the subject stationary in a field of view is imaged while the gratings are successively moved by the predetermined amount. Thus, imaging itself takes several tens to several hundreds of seconds at present.

On the other hand, subjects are successively conveyed by moving means such as a belt conveyor, for example, in a factory. When it is necessary to inspect all the subjects, the imaging of the subjects has to be completed in a short time and defects have to be detected at a high speed. A similar high-speed processing is necessary also in inspecting baggage at airports.

However, in the conventional fringe scanning method, a subject standing still at a predetermined position needs to be imaged a plurality of number of times using a two-dimensional X-ray image detector while shifting the grating by a fraction of an integer of a period of the grating. Thus, there has been a problem of being difficult to inspect subjects moving at a certain speed or higher.

Further, a mechanism for accurately shifting the grating by a very small amount requires considerable mechanical precision, which has presented a problem of imposing a burden in terms of cost and maintenance.

CITATION LIST

Patent Literature

Patent literature 1: International Publication No. WO2004/058070
Patent literature 2: Publication of U.S. Pat. No. 5,812,629
Patent literature 3: JP 2008-145111A
Patent literature 4: JP 2009-240378A Non-Patent Literature Non-patent literature 1: F. Pfeiffer et al., Nat. Phys. 2, 258-261 (2006)
Non-patent literature 2: A. Momose, S. Kawamoto, I. Koyama, Y. Hamaishi, K. Takai and Y. Suzuki, "Demonstration of X-ray Talbot interferometry," Jpn. J. Appl. Phys. 42, L866-L868 (2003)
Non-patent literature 3: M. Takeda, H. Ina and S. Kobayashi, "Fourier-transform method of fringe-pattern analysis for computer-based topography and interferometry," J. Opt. Soc. Am. 72, 156-160 (1982)
Non-patent literature 4: Atsushi Momose, Wataru Yashiro, Hirohide Maikusa, Yoshihiro Takeda, "High-speed X-ray phase imaging and X-ray phase tomography with Talbot interferometer and white synchrotron radiation," Opt. Express 17, 12540-12545 (2009)

BRIEF SUMMARY

The present disclosure was developed in view of the aforementioned situation, and provides a technology capable of conducting a high-sensitivity non-destructive inspection of a subject moving relative to a device using radioactive rays.

The present disclosure can be expressed as various embodiments as described in the following items.

(Item 1)

A non-destructive inspection device includes a radiation source unit, a grating group and a radioactive ray detector unit, wherein:

the radiation source unit is configured to irradiate radioactive rays having transmissivity to a subject toward the grating group;

the grating group is composed of a plurality of gratings capable of transmitting the radioactive rays irradiated toward the grating group; and each of the plurality of gratings includes a plurality of grating members arranged at a predetermined period determined for each grating;

the radioactive ray detector unit is configured to detect the radioactive rays diffracted by the plurality of grating members;

a radioactive ray passage area through which the radioactive rays irradiated from the radiation source unit and reaching the radioactive ray detector unit pass includes at least first to third partial areas;

the first to third partial areas are arranged at positions displaced from each other in a direction intersecting with an irradiation direction of the radioactive rays;

further, the first to third partial areas are located at such positions that the subject moving relative to the grating group passes in the direction intersecting with the irradiation direction of the radioactive rays; and when a part of the grating group located in a space through which each of the radioactive rays to be transmitted through any one of the first to third partial areas passes is called a reference grating partial group and parts of the grating group located in spaces through which the radioactive rays to be transmitted through the other ones of the first to third partial areas pass are respectively called first and second grating partial groups, the grating members of some of the gratings included in the reference grating partial group are arranged at the predetermined period in this grating, some of the gratings included in the first grating partial group includes a grating member having a first phase difference with respect to the arrangement at the predetermined period in some of these gratings and some of the gratings included in the second grating partial group includes a grating member having a second phase difference with respect to the arrangement at the predetermined period in some of these gratings.

(Item 2)

In the non-destructive inspection device according to item 1, each of the first to third partial areas includes a mutually overlapping part and a non-overlapping part;

the grating member having the first phase difference and the grating member having the second phase difference are both arranged in the non-overlapping parts; and the radiation source unit is configured to irradiate the radioactive rays to the first to third partial areas at different timings.

(Item 3)

In the non-destructive inspection device according to item 1 or 2, the radioactive ray detector unit is configured to detect the radioactive rays transmitted through the reference grating partial group, the radioactive rays transmitted through the first grating partial group and the radioactive rays transmitted through the second grating partial group.

(Item 4)

The non-destructive inspection device according to item 3 further includes a processing unit, wherein:

the processing unit is configured to calculate any one of an absorption image, a refraction image and a scattering image of the subject using detection values of the radioactive rays transmitted through the reference grating partial group, detection values of the radioactive rays transmitted through the first grating partial group and detection values of the radioactive rays transmitted through the second grating partial group.

(Item 5)

The non-destructive inspection device according to any one of items 1 to 4 further includes a conveying unit, wherein:

the conveying unit is configured to move the subject relative to the grating group in the direction intersecting with the irradiation direction of the radioactive rays.

(Item 6)

In the non-destructive inspection device according to any one of items 1 to 5, the grating group is composed of two gratings.

(Item 7)

In the non-destructive inspection device according to any one of items 1 to 5, the grating group is composed of three gratings.

(Item 8)

In the non-destructive inspection device according to any one of items 1 to 7, the radiation source unit includes first to third ray sources;

the first ray source is configured to irradiate the radioactive rays transmitted through the first partial area;

the second ray source is configured to irradiate the radioactive rays transmitted through the second partial area; and the third ray source is configured to irradiate the radioactive rays transmitted through the third partial area.

(Item 9)

In the non-destructive inspection device according to any one of items 1 to 8, the first and second phase differences are set at values capable of performing phase imaging using a detection result of the radioactive rays transmitted through the reference grating partial group, a detection result of the radioactive rays transmitted through the first grating partial group and a detection result of the radioactive rays transmitted through the second grating partial group.

(Item 10)

In the non-destructive inspection device according to any one of items 1 to 9, the radioactive rays are X-rays.

(Item 11)

A non-destructive inspection device includes a radiation source unit, a grating group and a radioactive ray detector unit, wherein:

the radiation source unit is configured to irradiate radioactive rays having transmissivity to a subject toward the grating group;

the grating group is composed of a plurality of gratings capable of transmitting the radioactive rays irradiated toward the grating group; and each of the plurality of gratings includes a plurality of grating members arranged at a predetermined period determined for each grating;

the radioactive ray detector unit is configured to detect the radioactive rays diffracted by the plurality of grating members;

a radioactive ray passage area through which the radioactive rays irradiated from the radiation source unit and reaching the radioactive ray detector unit pass includes at least first to third partial areas;

the first to third partial areas are arranged at positions displaced from each other in a direction intersecting with an irradiation direction of the radioactive rays;

further, the first to third partial areas are located at such positions that the subject relatively moving with respect to the grating group passes in the direction intersecting with the irradiation direction of the radioactive rays; and the plurality of grating members are arranged with a predetermined phase difference such that moiré patterns respectively formed by the radioactive rays transmitted through the first to third partial areas have phase differences between the moiré patterns.

(Item 12)

The non-destructive inspection device according to any one of items 1 to 11 further includes a driving unit, wherein:

the driving unit is configured to move the radiation source unit, the grating group and the radioactive ray detector unit as a whole relative to the subject in the direction intersecting with the irradiation direction of the radioactive rays.

(Item 13)

In the non-destructive inspection device according to any one of items 1 to 12, the subject is a living body.

(Item 14)

A medical image diagnosis device includes the non-destructive inspection device according to item 13 and an image presentation unit, wherein:

the image presentation unit is configured to present an absorption image, a refraction image or a scattering image obtained from information of the radioactive rays detected by the radioactive ray detector unit as an image for diagnosis.

(Item 15)

A non-destructive inspection method using the non-destructive inspection device according to any one of items 1 to 13 includes:

a step of moving the subject relative to the grating group in the direction intersecting with the irradiation direction of the radioactive rays;

a step of detecting the radioactive rays transmitted through the subject when the subject passes through the reference grating partial group;

a step of detecting the radioactive rays transmitted through the subject when the subject passes through the first grating partial group; and a step of detecting the radioactive rays transmitted through the subject when the subject passes through the second grating partial group.

According to the present disclosure, it becomes possible to conduct a high-sensitivity non-destructive inspection of a subject moving relative to a device using radioactive rays.

BRIEF DESCRIPTION OF DRAWINGS

FIGS. 3(a) and 3(b) show an arrangement pattern of grating members, wherein FIG. 3(a) is a plan view of a grating and FIG. 3(b) is a graph showing profiles of grating members on a transverse section of the grating of FIG. 3(a), a horizontal axis representing a position in a width direction of the grating and a vertical axis representing a height from a bottom surface of the grating in FIG. 3(b), FIG. 6 is a table showing operational expressions for computing specified images from image data, FIGS. 7(a) and 7(b) show an example of a grating used in a non-destructive inspection device according to a second embodiment of the present invention, wherein FIG. 7(a) is a plan view of the grating and FIG. 7(b) is a diagram enlargedly showing an arrangement pattern of grating members, FIGS. 8(a) and 8(b) are diagrams showing the operation of a modification of a non-destructive inspection device according to a third embodiment of the present invention.

DETAILED DESCRIPTION (Configuration of Non-Destructive Inspection Device in First Embodiment)

Hereinafter, the configuration of a non-destructive inspection device according to a first embodiment of the present invention is described with reference to the drawings.

(Overall Configuration of Non-Destructive Inspection Device)

Figure 1:
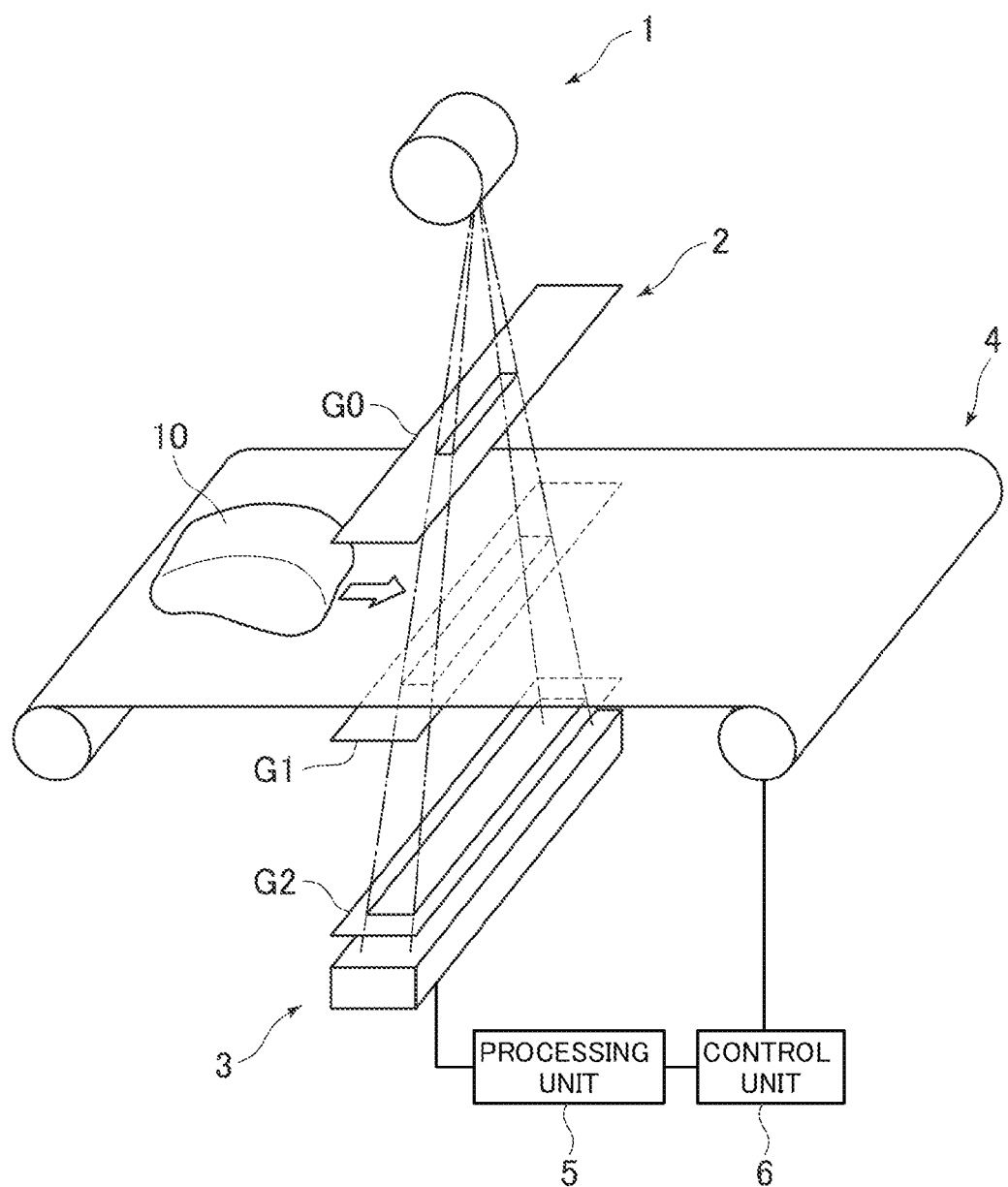
FIG. 1 is a diagram showing a schematic configuration of a non-destructive inspection device according to a first embodiment of the present invention.

The non-destructive inspection device of the present embodiment includes a radiation source unit 1, a grating group 2 and a radioactive ray detector unit 3 (see FIG. 1). Further, this non-destructive inspection device additionally includes a conveying unit 4, a processing unit 5 and a control unit 6.

(Radiation Source Unit)

The radiation source unit 1 is configured to irradiate radioactive rays having transmissivity to a subject 10 toward the grating group 2. Specifically, in the present embodiment, an X-ray source unit for generating X-rays is used as the radiation source unit 1. An X-ray source unit for generating X-rays (i.e., radioactive rays) by irradiating electron beams to a target can be, for example, used as the radiation source unit 1. A specific configuration of the radiation source unit 1 is not described in any further detail since it can be the same as existing X-ray source units.

(Grating Group)

The grating group 2 includes a plurality of gratings through which radioactive rays irradiated toward this grating group 2 can be transmitted. The grating group 2 satisfies conditions for a mechanical structure and a geometric arrangement necessary to configure a Talbot interferometer (including a case of a Talbot-Lau interferometer). However, in the present embodiment, the conditions for configuring a Talbot interferometer have only to be satisfied to a degree sufficient to enable a necessary inspection and need not be satisfied in a mathematically strict sense.

Specifically, the grating group 2 of the present embodiment is configured by three gratings including a grating G0, a grating G1 and a grating G2. The grating G0 is a grating for configuring a Talbot-Lau interferometer which is one type of the Talbot interferometer and an absorption type grating is used. A minute radiation source array, which is a constituent element of the Talbot-Lau interferometer, is realized by the grating G0. Although a phase type grating is normally used as the grating G1, it is also possible to use an absorption type grating. An absorption type grating is used as the grating G2. It should be noted that the arrangement of G2 can also be omitted (Lau interferometer, see JP2012-16370A).

Each of the gratings G0 to G2 includes a plurality of grating members 21 (see FIG. 3) arranged at a predetermined period determined for each grating. This predetermined period is geometrically calculated to configure a Talbot-Lau interferometer. Generally, the predetermined period differs if a distance from a ray source to a grating differs. Since a calculation method for such a predetermined period is conventionally known (see, for example, patent literature 3, 4 described above), it is not described in detail. It should be noted that the grating members 21 constituting the grating may be integrated with other members and need not be present as independent members. In short, the grating members 21 are not particularly restricted in configuration if being structured to give a necessary periodic modulation to used radioactive rays.

(Radioactive Ray Detector Unit)

The radioactive ray detector unit 3 is configured to detect the radioactive rays arriving thereat after being transmitted through the plurality of grating G0 to G2 pixel by pixel. Specifically, an X-ray line sensor capable of detecting X-rays by each of pixels arranged in a one-dimensional direction is used as the radioactive ray detector unit 3 of the present embodiment. More specifically, this radioactive ray detector unit 3 includes detectors 31 to 33 (see FIG. 2). Each detector 31 to 33 extends in a thickness direction of the plane of FIG. 2 and configures a line sensor. That is, the radioactive ray detector unit 3 of the present embodiment is a three-row X-ray line sensor. The detector 31 is configured to detect the radioactive rays transmitted through a reference grating partial group 220 (described later), the detector 32 is configured to detect the radioactive rays transmitted through a first grating partial group 221 (described later) and the detector 33 is configured to detect the radioactive rays transmitted through a second grating partial group 222 (described later).

It should be noted that two-dimensional image data of the subject can be obtained by arranging obtained one-dimensional data in time series in line sensors. The line sensors described here include not only sensors in which pixels are one-dimensionally arranged, but also sensors of a type that the sum of pixel values at corresponding pixel positions are read in synchronization with a motion of a subject for a pixel row of a direction of the motion of the subject using a two-dimensional sensor such as TDI (Time Domain Integration) detectors and sensors of a type that a TDI motion is simulated by computer computation after two-dimensional images are read at a high speed.

Figure 2:
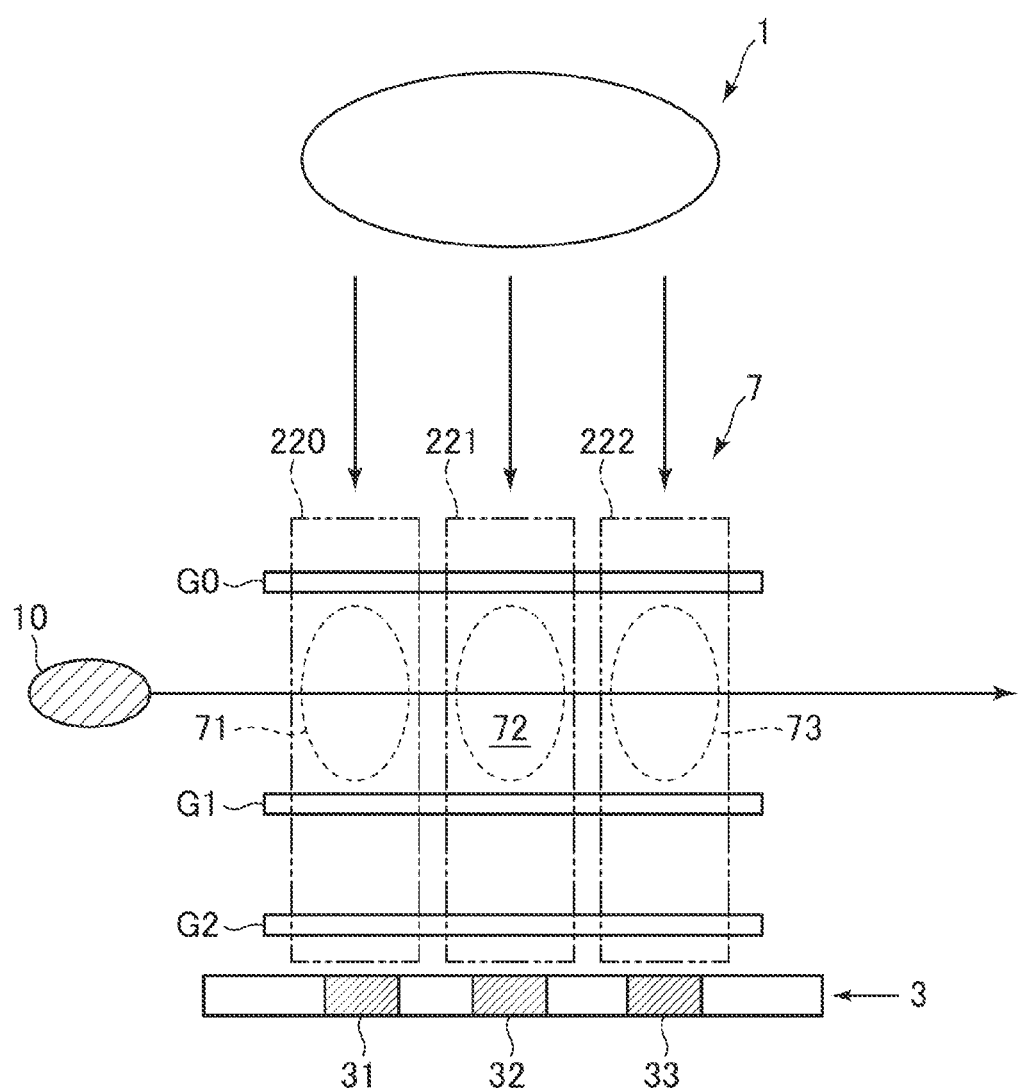
FIG. 2 is a schematic diagram of the non-destructive inspection device of FIG. 1 when cut along a plane extending along a moving direction of a subject.

Further, an irradiation direction of X-rays is shown assuming approximately plane-wave X-rays in FIG. 2.

(Configuration for Giving Phase Difference Between Grating Members)

Here, a configuration for giving a phase difference between the grating members, which is a characteristic of the present embodiment, is described. For this description, an area where the radioactive rays irradiated from the radiation source unit 1 and reaching the radioactive ray detector unit 3 pass is referred to as a radioactive ray passage area 7 in the present embodiment. This radioactive ray passage area 7 means a space from the radiation source unit 1 to the radioactive ray detector unit 3 in this embodiment. This radioactive ray passage area 7 includes first to third partial areas 71 to 73 (shown in broken lines in FIG. 2). These partial areas are virtual areas only for description. It should be noted that the shapes of these partial areas are not particularly restricted.

The first to third partial areas 71 to 73 are arranged at positions displaced from each other in a direction intersecting with an irradiation direction of the radioactive rays (transverse direction in FIG. 2 in this example).

Further, the first to third partial areas 71 to 73 are located at such positions that the subject 10 moving relative to the grating group 2 can pass in the direction (transverse direction in FIG. 2 in this example) intersecting with the irradiation direction of the radioactive rays. More specifically, the first to third partial areas 71 to 73 are located between the gratings G0 and G1. It should be noted that although the first to third partial areas 71 to 73 are successively arranged from left in FIG. 2, there is no order restriction. Similarly, notation such as first, second, . . . , $n^{th}$ in this specification is not for restricting the order, but for mutual distinction.

Further, in the present embodiment, a concept of reference, first and second grating partial groups is introduced as described below for description. Each partial group is at least a partial set of the gratings G0 to G2 constituting the grating group 2.

Specifically, a part of the grating group 2 located in a space where the radioactive rays that should pass any one of the first to third partial areas 71 to 73 (first partial area in the shown example) is called the reference partial group 220 (grating in a part enclosed by a broken line 220 in FIG. 2). A part of the grating group 2 located in a space where the radioactive rays that should pass another one of the first to third partial areas 71 to 73 (second partial area in the shown example) is called the first partial group 221 (grating in a part enclosed by a broken line 221 in FIG. 2). A part of the grating group 2 located in a space where the radioactive rays that should pass still another one of the first to third partial areas 71 to 73 (third partial area in the shown example) is called the second partial group 222 (grating in a part enclosed by a broken line 222 in FIG. 2). An arrangement order of the reference partial group 220 and the first and second partial groups 221, 222 described above is also not particularly restricted.

As a premise, the grating members 21 in a part of each grating G0 to G2 included in each partial group 220 to 222 are arranged at a predetermined period to satisfy the configuration of a Talbot interferometer. Thus, the grating members 21 in the parts of the gratings G0 to G2 included in the reference partial group 220 are also arranged at the predetermined period in these gratings. The period of the grating members 21 included in the reference partial group 220 serves as a reference of the phase difference described below.

Figure 3:
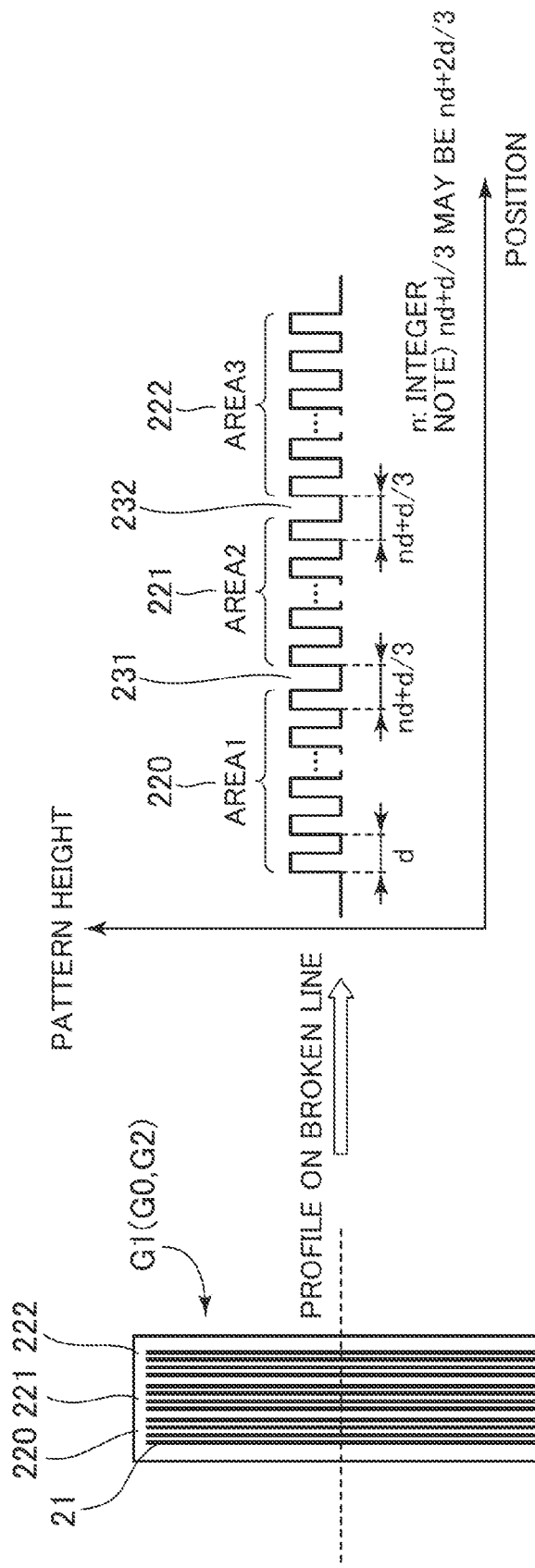

An example in which a plurality of reference grating members 21 and a plurality of grating members shifted in phase (described later) are arranged on one of the gratings G0 to G2 (e.g., grating G1) is shown in FIG. 3. Denoted by 220 in FIG. 3 are the grating members 21 included in the reference partial group 220. Similarly, denoted by 221 in FIG. 3 are the grating members 21 included in the first partial group 221 and denoted by 222 are the grating members 21 included in the second partial group 222. Note that each grating member 21 extends in the longer direction of the grating G1 in the shown example.

A partial grating included in the first grating partial group 221 (part of the grating G1 in the example of FIG. 3) includes a first phase shift section 231 for giving a first phase difference (described later) to the arrangement of the grating members 21 to be arranged at the predetermined period in this partial grating. Specifically, the grating members included in the first grating partial group 221 satisfy the predetermined period required for Talbot-Lau interferometer, but a phase difference of a specified amount with respect to the grating members included in the reference grating partial group 220 is set for the phase of the grating members included in the first grating partial group 221. An example of the first phase shift section 231 is shown in FIG. 3($b$). In this example, d denotes the predetermined period. A part having a period of nd+d/3 in FIG. 3($b$) is the first phase shift section, where n is an integer. That is, the phase is shifted by d/3. A phase shift amount determination technique is described later. It should be noted that the phase shift section in this specification has only to be a part capable of forming a phase difference as described above and may be a simple space. Here, although the grating G1 is taken as an example above, a phase-shifted grating member can be provided in the grating G0 or G2 instead of this.

Similarly to the above, a partial grating included in the second grating partial group 222 (part of the grating G1 in the example of FIG. 3) includes a second phase shift section 232 for giving a second phase difference (described later) to the arrangement of the grating members to be arranged at the predetermined period in this partial grating (see FIG. 3(*b*)). The second phase shift section 232 further gives a phase difference of d/3, to the grating members 21, in addition to the phase difference in the first phase shift section 231. Thus, a phase difference of 2d/3 is given as compared with the grating members in the reference grating partial group 220. It should be noted that the setting of each of the phase shift amounts in the first and second phase shift sections to 2d/3 is equivalent in principle to the aforementioned phase difference. Further, similarly to the above, a phase-shifted grating member can be provided to give a phase difference of 2d/3 in the grating G0 or G2 instead of the grating G1.

(Phase Shift Amount Determination Method)

The first and second phase differences are set at values capable of performing a phase imaging method using a detection result of the radioactive rays transmitted through the reference grating partial group 220, a detection result of the radioactive rays transmitted through the first grating partial group 221 and a detection result of the radioactive rays transmitted through the second grating partial group 222.

In the conventional fringe scanning method, a plurality of images are obtained by parallelly moving a grating in each step of 1/M (M is an integer not smaller than 3) of the period of the grating. At this time, moiré patterns formed by a self-image of the grating G1 and the grating G2 are obtained as intensity distributions of radioactive rays by the radioactive ray detector unit 3. Further, the moiré pattern periodically changes in accordance with a movement amount of the grating. When the grating moves an amount corresponding to one period, the moiré pattern returns to an original shape. Accordingly, the so-called phase imaging method (process of obtaining an absorption image, refraction image or scattering image) can be performed utilizing M images corresponding to a step number M of the grating.

The conventional fringe scanning method can be applied to substantially stationary subjects. To apply a conventional measurement to a subject moving as a target in the present embodiment, the fringe scanning method has to be performed at a very high speed, including minute step movements of a grating and it is difficult to perform such a method. The present embodiment can be said to be a method for performing a fringe scanning method, utilizing a movement of the subject. Specifically, areas corresponding to minute step movements of a grating are spatially arranged and formed and the acquisition of data necessary for the fringe scanning method is realized by causing the subject to pass through those areas. Thus, a phase difference is given between the grating members of each grating so that a specified phase difference can be generated between moiré pattern images formed by the radioactive rays incident on the detectors 31 to 33 of the radioactive ray detector unit 3. Here, there is almost no structural restriction for the positions of the grating members for giving a phase difference. For example, an appropriate design is possible such as by giving a phase difference to the grating member of the grating G0 in a radioactive rays passage part for the radioactive rays to be incident on the detector 32 and giving a phase difference to the grating member of the grating G1 in the radioactive rays passage part for the radioactive rays to be incident on the detector 33. In short, a plurality of grating members have only to be arranged with the specified phase difference so as to "provide a phase difference between moiré patterns each formed by the radioactive rays transmitted through the first to third partial areas 71 to 73."

Further, the number of the gratings constituting the grating group 2 may be two by excluding the grating G0 or G2 (design conditions in the case of a two-grating configuration is also already known). In this case, a phase shift has only to be made in each area as described above in the grating members constituting the two gratings.

The calculation of the phase shift amount is described in more detail. When p denotes the number of the partial areas described above (i.e., the number of the first to $n^{th}$ partial areas) and i denotes each integer satisfying $1 \leq i \leq (p-1)$, the arrangement of the grating members in any one of the gratings present in the $i^{th}$ grating partial group has a phase difference obtained by $(d/p) \times i$ with respect to the arrangement of the gratings at the predetermined period (i.e., predetermined period in the gratings belonging to the reference grating partial group). It should be noted that this phase difference need not be mathematically strict and a slight error is allowed if this condition is satisfied to a practically problem-free degree. Here, d is a periodical configuration in the grating, i.e., an arrangement period of the grating members and p has generally an integer value not smaller than 3. Further, the number q of the grating partial groups including the reference grating partial group is not smaller than a division number p of the period, i.e., $q \geq p$. Specifically, it is possible that the grating partial groups capable of forming a phase difference between the moiré images are present more than necessary (i.e., redundant areas are present).

It should be noted that the grating members other than those with the phase difference are arranged in a periodic structure without a phase difference in the gratings present in the $i^{th}$ grating partial group.

Further, since the phase differences are, in principle, equivalent even if an N-fold period (N is an integer other than 0) is added, the phase differences include those with the N-fold period.

(Conveying Unit)

The conveying unit 4 is configured to move the subject 10 relative to the grating group 2 in the direction intersecting with the irradiation direction of the radioactive rays (transverse direction in FIGS. 1 and 2). Specifically, the conveying unit 4 of the present embodiment is configured by a belt conveyor for moving the subject 10 in the transverse direction. Further, the conveying unit 4 conveys this subject 10 so that the subject 10 can pass through a space between the gratings G0 and G1 where the radioactive rays are transmitted. It should be noted that the conveying unit 4 may pass the subject 10 between the gratings G1 and G2. It should be noted that the subject 10 is caused to pass between the grating G1 and the radioactive ray detector unit 3 in the case of the configuration of a Lau interferometer (see JP 2012-16370A).

A belt used in the belt conveyor as the conveying unit 4 is preferably selected to have high transmissivity to radioactive rays used, but is not particularly restricted if a structure and a material used in ordinary conveyors are used. It should be noted that, without limitation to the belt conveyor, the conveying unit 4 can be appropriately configured if it can convey the subject 10 in a desired direction. Further, a configuration for fixing the subject 10 and relatively moving the entire assembly of the radiation source unit, the grating group and the radioactive ray detector unit with respect to the subject 10 (including a movement on a polar coordinate) is also theoretically possible.

(Processing Unit)

The processing unit 5 is configured to calculate any one or all of the absorption image, the refraction image and the scattering image of the subject using detection values (i.e., image data) of the radioactive rays transmitted through the reference grating partial group 220, detection values of the radioactive rays transmitted through the first grating partial group 221 and detection values of the radioactive rays transmitted through the second grating partial group 222. A specific calculation method is described later as the operation of the non-destructive inspection device of the present embodiment.

(Control Unit)

The control unit 6 is configured to send a drive signal to the conveying unit 4 and send moving speed information (indication value or detection value) of the subject 10 to the processing unit 5.

(Operation of Non-Destructive Inspection Device of Present Embodiment)

The operation of the non-destructive inspection device of the present embodiment is described below further with reference to FIG. 4.

Figure 4:
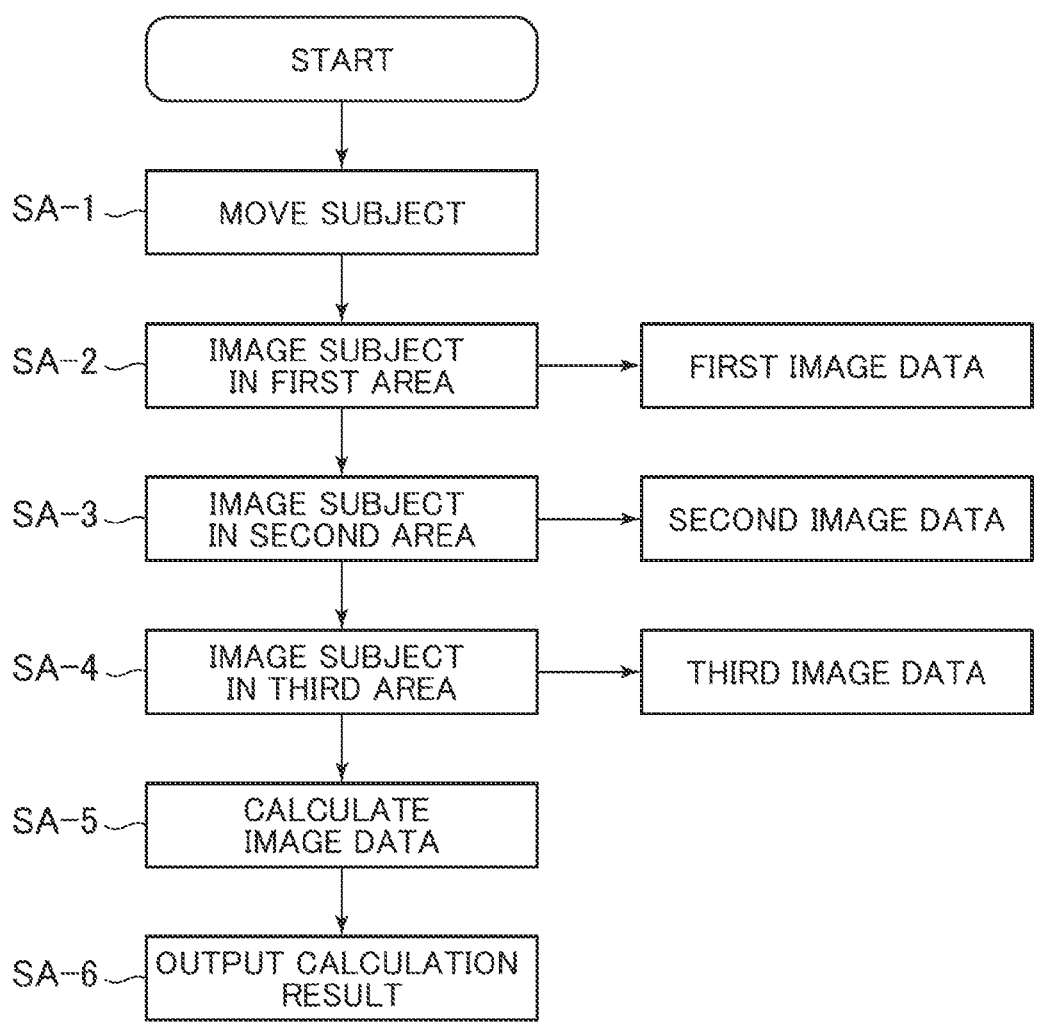
FIG. 4 is a flow chart schematically showing an inspection method using the non-destructive inspection device of FIG. 1.

(Step SA-1 of FIG. 4)

A state where radioactive rays are irradiated from the radiation source unit 1 toward the radioactive ray detector unit 3 is considered as an initial state. In this state, the subject 10 is conveyed in a specified direction by the conveying unit 4 on the basis of a control command from the control unit 6. The control unit 6 sends a moving speed of the subject 10 to the processing unit 5. The radioactive ray detector unit 3 is in a state where detection signals are continuously recorded in time series.

(Steps SA-2 to 4 of FIG. 4)

Subsequently, the subject 10 moves to between the detector 31 of the radioactive ray detector unit 3 and the radiation source unit 1 and the radioactive ray detector unit 3 detects an radioactive rays intensity at each pixel position in time series by the detector 31, obtains first image data $I_1(x, t)$ and, simultaneously, outputs it to the processing unit 5 (see FIG. 5).

Figure 5:
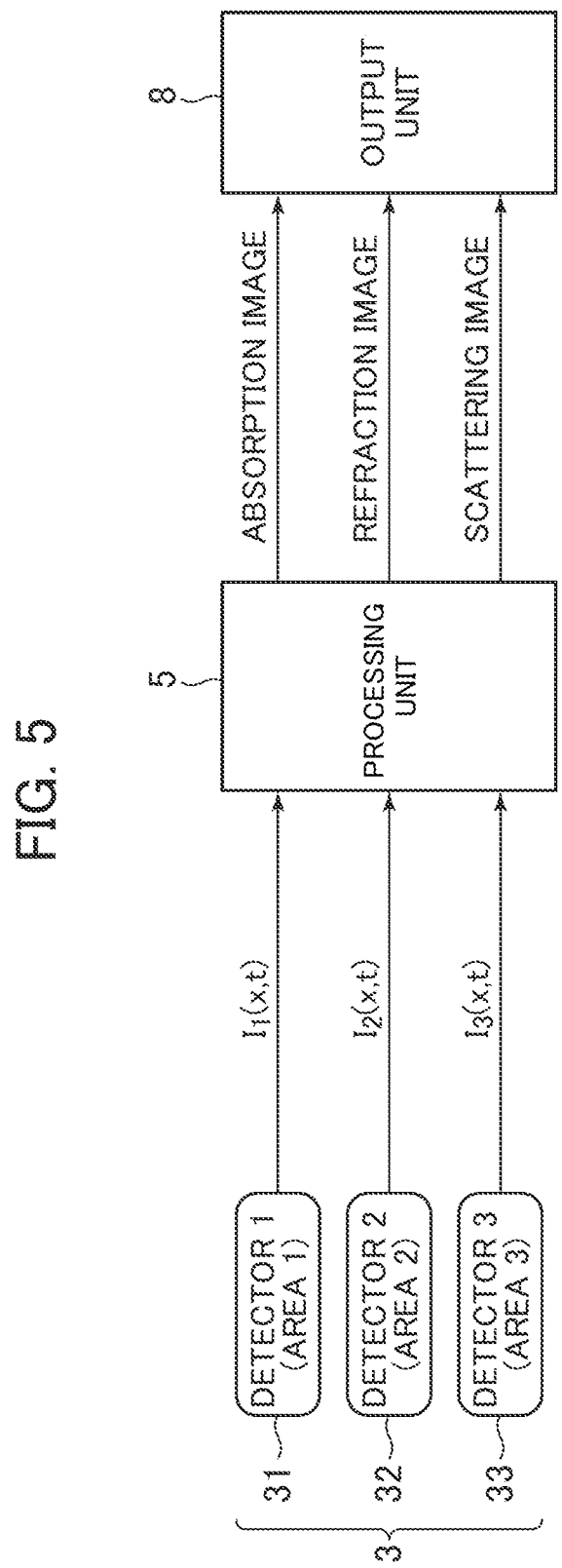
FIG. 5 is a diagram showing an image data arithmetic processing method.

Thereafter, similarly, the subject 10 is recorded as $I_2(x, t)$ and $I_3(x, t)$ in the detectors 32, 33 and $I_2(x, t)$ and $I_3(x, t)$ are output to the processing unit 5 according to a movement of the subject 10 (see FIG. 5). It should be noted that Steps SA-2 to SA-4 are not necessarily such that the succeeding step is performed after one step is completed. For example, if the subject 10 is large, there are cases where these steps are performed in parallel such that a part of the subject 10 is imaged by the detector 31 while another part is imaged by the detector 32.

(Step SA-5 of FIG. 4)

Subsequently, the calculation method in the processing unit 5 is described further with reference to FIG. 6. As a premise, $\tau_a$, $\tau_b$ denote time differences between a time at which a certain part of the subject 10 is recorded by the detector 31 and times at which the same part are recorded by the detectors 32 and 33. The time differences $\tau_a$, $\tau_b$ can be calculated from the speed information (subject moving speed information) obtained from the conveying unit 4 by the processing unit 5.

Then, the absorption image, the refraction image and the scattering image can be calculated by a left column of FIG. 6 (column of "Device without Correction") using the image data $I_1$ to $I_3$ (so-called phase imaging method). Here, the definition of S(x, t) is as shown in FIG. 6. Further, arg[S(x, t)] is a function indicating an argument of S(x, t). It should be noted that the number of pieces of the image data I coincides with a denominator p of the phase difference described above if redundancy is not considered. Even if the number of pieces of the image data I is 4 or more, the principle of the phase imaging process is the same as described above.

Further, when image data $I^0$ similarly measured in the absence of the subject 10 is obtained, each image can be calculated by expressions shown in a right column of FIG. 6. In this way, a contrast component caused by a mechanical error of the device and the like can be subtracted and there is an advantage of being able to obtain more accurate images.

(Step SA-6 of FIG. 4)

Subsequently, the processing unit 5 outputs the obtained time-series images (absorption images, refraction images or scattering images) to an output unit 8. Of course, the processing unit 5 can record the obtained images in a recording unit (not shown) instead of or in addition to the output to the output unit 8. An output destination of the images by the processing unit 5 can be appropriately selected according to the purpose of the device. The output unit 8 is, for example, a display or a printer, but may be, for example, another system utilizing processing results without being restricted to those.

Since a certain scanning time is required to obtain a plurality of images accompanying the step-wise movements of a grating in a non-destructive inspection using the phase imaging method (particularly the one using the conventional fringe scanning method), there has been a problem of being unsuitable for the inspection of moving subjects.

Contrary to this, in the present embodiment, the movement of the subject 10 is utilized without moving the gratings. This enables the images of the subject successively passing through the first to third partial areas 71 to 73 to be obtained by each linear detector 31 to 33. Using these images, the necessary phase imaging process can be performed as described above.

Thus, according to the non-destructive inspection device of the present embodiment, there is an advantage of enabling a high-sensitivity non-destructive inspection of the moving subject 10 making use of the movement of the subject 10.

Further, since a driving mechanism for precisely driving the gratings can be omitted in the present embodiment, the production, installation and maintenance of the device can be simplified, which can contribute to the reduction of cost including running cost. Furthermore, it is believed that an installation space of the entire device can be reduced in size.

(Second Embodiment)

Figures 7A, 7B:
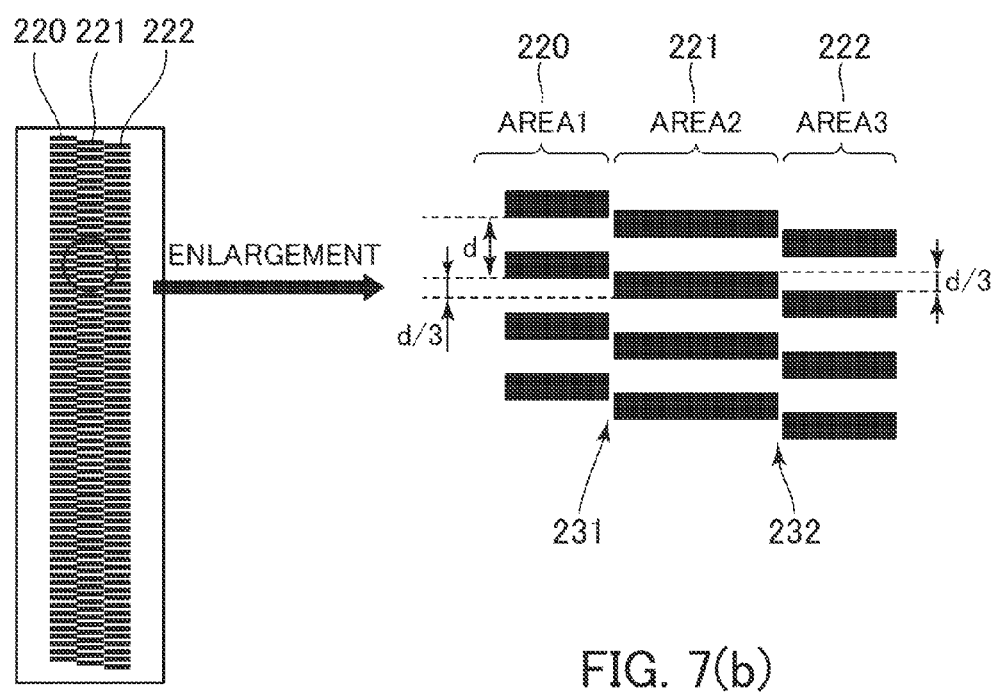

Next, a non-destructive inspection device according to a second embodiment of the present invention is described on the basis of FIG. 7. It should be noted that elements basically common to those of the first embodiment are denoted by the same reference signs in the description of the second embodiment to avoid repeated description.

In the first embodiment described above, each grating member 21 included in each grating G0 to G2 extends in the longer direction of each grating (thickness direction of the plane of FIG. 2, vertical direction in FIG. 3). Contrary to this, in the non-destructive inspection device of the second embodiment, each grating member 21 extends in the shorter direction of each grating (lateral direction in FIG. 7). Here, in FIG. 7, grating members included in each grating partial group 220 to 222 are respectively denoted by reference signs 220 to 222. As is understood from this, the grating members in an area included in the reference grating partial group 220 have a predetermined period d. The grating members in an area included in the first grating partial group 221 has a phase difference of d/3 with respect to the grating members of the reference grating partial group 220 while having the predetermined period d. Further, the grating members in an area included in the second grating partial group 222 has a phase difference of d/3 with respect to the grating members of the first grating partial group 221 (2d/3 with respect to the grating members of the reference grating partial group 220) while having the predetermined period d.

The operation of the non-destructive inspection device of the second embodiment is basically the same as in the case of the first embodiment. Specifically, radiation image data $I_1$ to $I_3$ in each area is obtained according to a movement of a subject 10 and a desired subject image can be generated from those pieces of the image data.

Further, the non-destructive inspection device of the second embodiment has an advantage of being able to increase an effective thickness of the grating members by inclining the gratings in the shorter direction of the gratings (lateral direction of FIG. 7). If the gratings are inclined (see FIG. 8(b)), the ranges of the radioactive rays capable of being transmitted through the gratings are narrowed as compared to the case where the gratings are not inclined (see FIG. 8(a)). This is not preferable since an imaging field of view is narrowed in the case of using a conventional two-dimensional sensor (or in the case of inclining the gratings of FIG. 3 in a vertical direction of FIG. 3 in the first embodiment). Contrary to this, in the present embodiment using a linear sensor as a radioactive ray detector 3, pixels are arranged in the width direction of a conveying unit 4 even if the gratings shown in FIG. 7 are inclined in the lateral direction of FIG. 7. Thus, an imaging field of view of the line sensor is not reduced. In the case of using high-energy X-rays, an improvement of an aspect ratio of the grating members of the gratings G0 and G2 is necessary, but difficulty in production technology is expected. Contrary to this, in the second embodiment, this difficulty can be overcome by arranging the gratings in an inclined manner as described above.

Other configurations and advantages of the second embodiment are not described in any further detail since being similar to those of the first embodiment described above.

(Third Embodiment)

Figure 9:
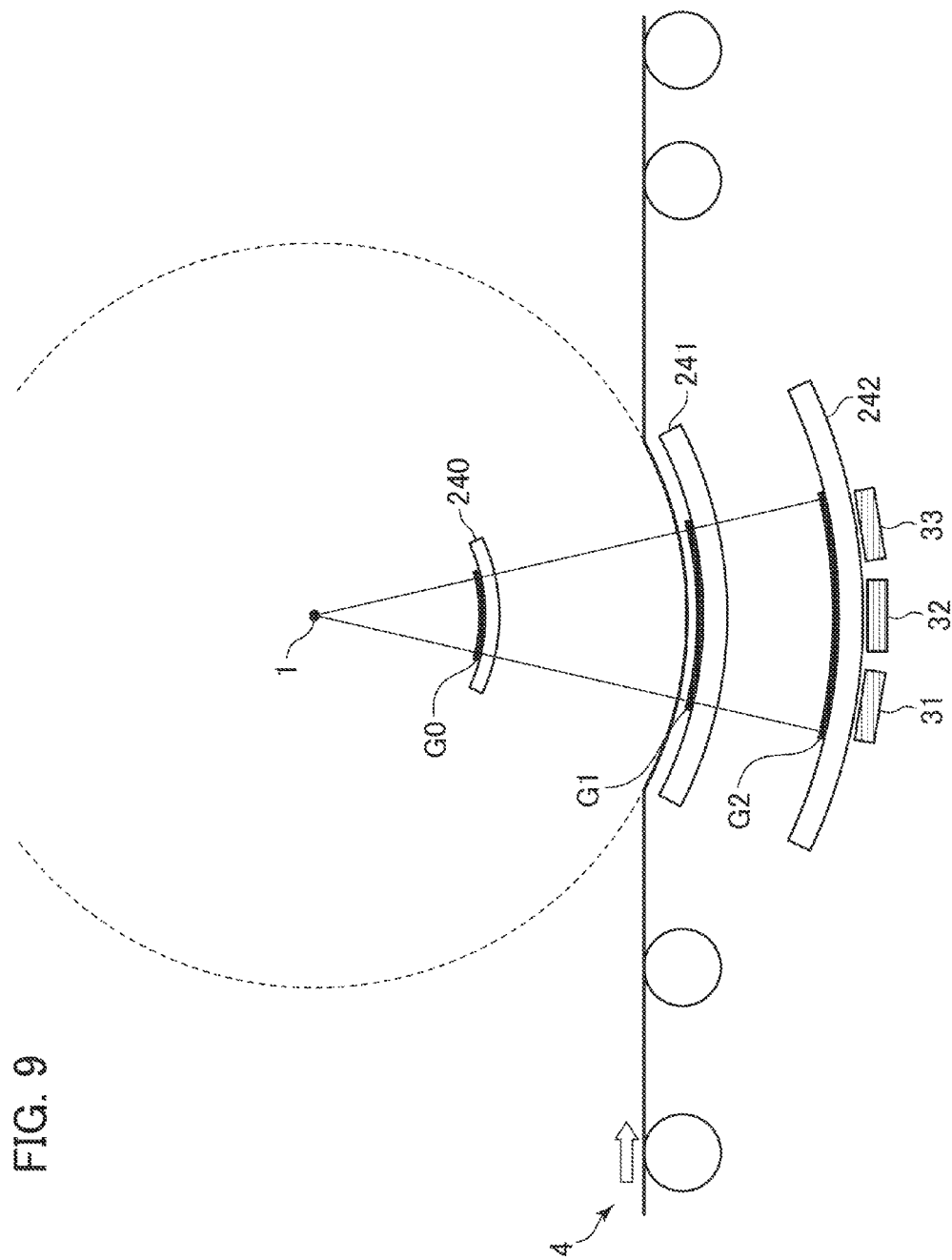
FIG. 9 is a schematic diagram of the non-destructive inspection device according to the third embodiment of the present invention in a plane extending along a moving direction of a subject.

Next, a non-destructive inspection device according to a third embodiment of the present invention is described on the basis of FIG. 9. It should be noted that elements basically common to those of the first embodiment are denoted by the same reference signs in the description of the third embodiment to avoid repeated description.

In the first embodiment described above, the subject 10 makes a translational movement. At this time, angles of intersection of the radioactive rays reaching the detectors 31 to 33 constituting the radioactive ray detector unit 3 from the radiation source unit 1 with the subject 10 are slightly different. This becomes a cause of an error in the calculation of the phase imaging method. Particularly, this problem becomes bigger as the subject 10 becomes thicker. In the present embodiment, a conveying unit 4 having an arcuate course centered on a radiation source unit 1 is provided to avoid this problem. The subject 10 moves while being kept at a fixed distance from the radiation source unit 1 and constantly facing in the same direction toward the radiation source unit 1. This makes paths of radioactive rays transmitted to the subject 10 constantly fixed and enables a calculation error in the phase imaging method to be reduced, with the result that bad influences (e.g., image blurring) due to the calculation error can be avoided. Further, in the first embodiment described above, each grating G0 to G2 constituting the grating group 2 is in the form of a flat plate. In the case of adopting the conveying unit 4 having an arcuate course, an error due to this cannot be ignored in the calculation of phase imaging. Accordingly, in the non-destructive inspection device of the third embodiment, each grating G0 to G2 is arranged in a curved manner concentrically with the radiation source unit 1 as a center.

More specifically, the non-destructive inspection device of the third embodiment includes a G0 holder 240, a G1 holder 241 and a G2 holder 242. As shown in FIG. 9, each holder 240 to 242 has a concentric cylindrical surface centered on the radiation source unit 1 (an example of a concentric circle is virtually shown in broken line in FIG. 9). As a result, each grating G0 to G2 is concentrically held with the radiation source unit 1 as a center. It should be noted that each grating G0 to G2 can be configured by a combination of three partial gratings separated from each other and the partial gratings can be approximately substituted by plate gratings. At any rate, a geometric arrangement including an arrangement period of grating members 21 included in each partial grating satisfies conditions for configuring a Talbot interferometer as in the above embodiments.

Further, detectors 31 to 33 constituting a radioactive ray detector unit 3 of the present embodiment are arranged immediately behind the G2 holder 242. Each detector 31 to 33 is arranged on a concentric circle centered on the radiation source unit 1, whereby a distance between the grating G2 and each detector 31 to 33 is constant.

The operation of the non-destructive inspection device of the third embodiment is also basically the same as the example of the first embodiment. Specifically, radiation image data $I_1$ to $I_3$ in each area is obtained and desired subject images can be generated from those pieces of the image data.

Since the other configurations and advantages in the third embodiment are similar to those of the first embodiment described above, they are not described in any further detail.

(Fourth Embodiment)

Figure 10:
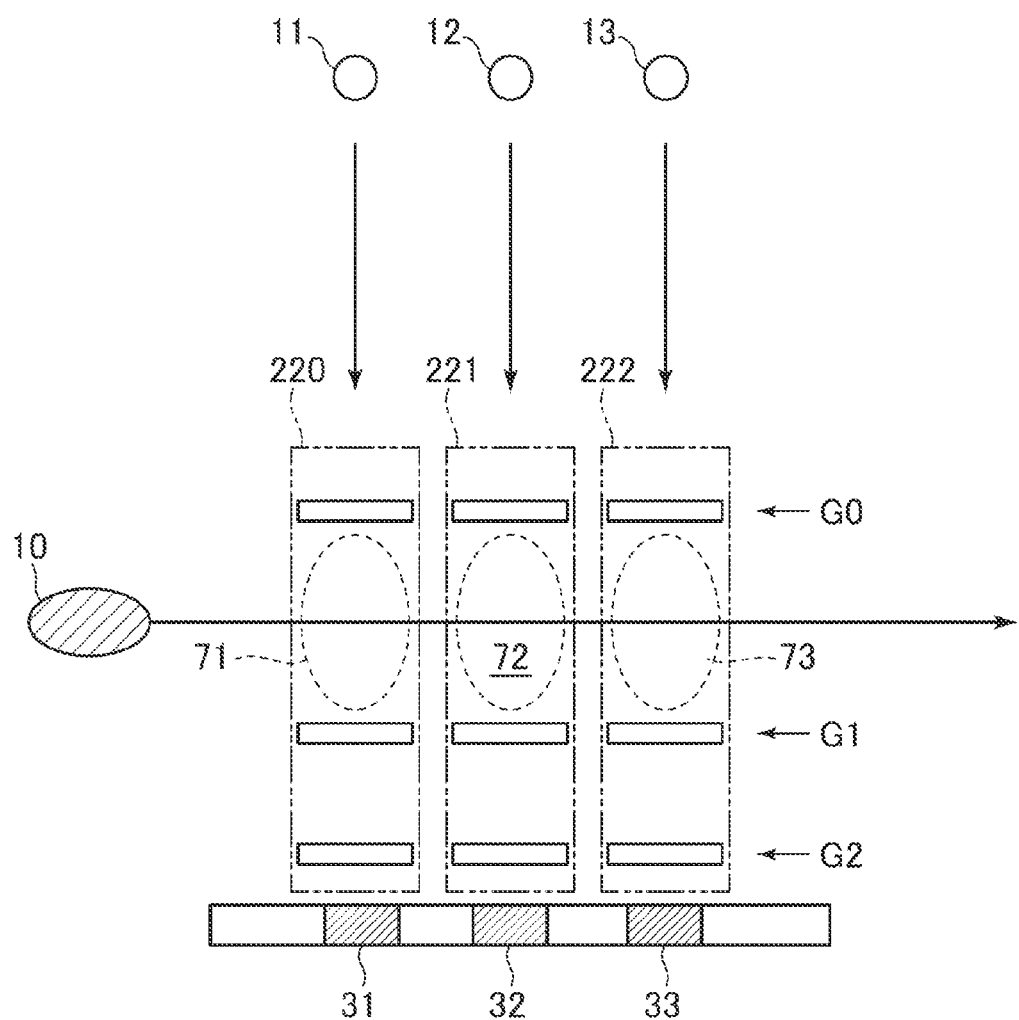
FIG. 10 is a schematic diagram of a non-destructive inspection device according to a fourth embodiment of the present invention in a plane extending along a moving direction of a subject.

Next, a non-destructive inspection device according to a fourth embodiment of the present invention is described on the basis of FIG. 10. It should be noted that elements basically common to those of the embodiments described above are denoted by the same reference signs in the description of the fourth embodiment to avoid repeated description.

In the first embodiment described above, radioactive rays are irradiated from a single ray source. Contrary to this, in the non-destructive inspection device of the fourth embodiment, a radiation source unit 1 includes first to third ray source 11 to 13 (see FIG. 10) and radioactive rays are irradiated toward corresponding radioactive ray detectors 31 to 33 from the respective ray source 11 to 13. Specifically, the first ray source 11 irradiates radioactive rays to be transmitted through a first partial area 71, the second ray source 12 irradiates radioactive rays to be transmitted through a second partial area 72 and the third ray source 13 irradiates radioactive rays to be transmitted through a third partial area 73.

Further, in the present embodiment, each grating G0 to G2 is configured by a combination of separate three partial gratings. Also in these partial gratings, a geometric arrangement including an arrangement period of grating members 21 included therein satisfies conditions for configuring a Talbot interferometer. Specifically, the grating members 21 constituting a grating group 2 of this fourth embodiment are arranged with a predetermined phase difference as in the above embodiments. For example, partial gratings constituting a grating G0 can be arranged such that the grating members of the left partial grating in FIG. 10 have a phase difference of 0, the grating members of the middle partial grating have a phase difference of d/3 and the grating members on the right side have a phase difference of 2d/3. However, as in the above embodiments, it is also possible to give a phase difference between different gratings. For example, the grating members can be arranged such that all the grating members of the grating G0 have a phase difference of 0, only the grating members of the middle partial grating in the grating G1 have a phase difference of d/3 and only the grating members on the right side in the grating G2 have a phase difference of 2d/3. In the fourth embodiment, it can be grasped that the left partial gratings of the gratings G0 to G2 constitute a reference grating partial group 220, the middle partial gratings of the gratings G0 to G2 constitute a first grating partial group 221 and the right partial gratings of the gratings G0 to G2 constitute a second grating partial group 222.

The operation of the non-destructive inspection device of the fourth embodiment is also basically the same as the example of the first embodiment. Specifically, radiation image data $I_1$ to $I_3$ in each area is obtained according to a movement of the subject 10 and desired subject images can be generated from those pieces of the image data.

Since angles of the radioactive rays irradiated to the subject 10 can be constant in each partial area in the fourth embodiment, an improvement of the accuracy of images generated by the phase imaging method can be expected.

Figure 11:
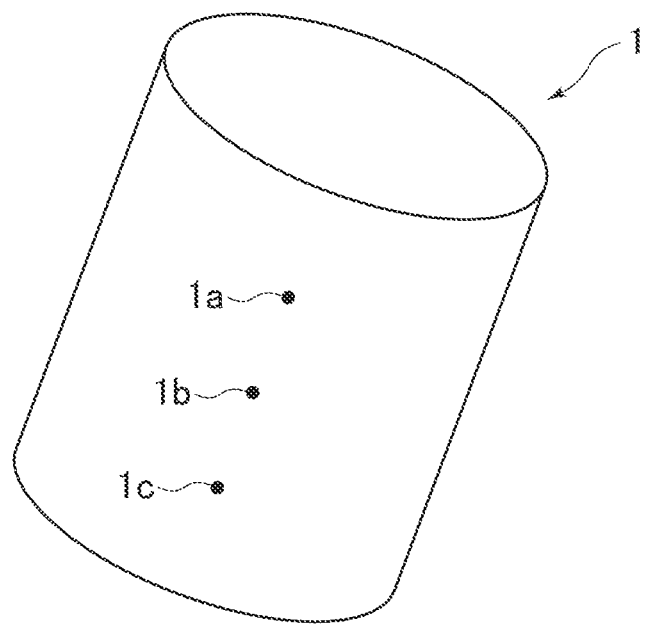
FIG. 11 is a diagram showing a configuration example of an X-ray source unit in the non-destructive inspection device of FIG. 10.

It should be noted that separate targets need not be used to configure the radiation source unit 1 shown in FIG. 10. For example, three radioactive ray generation can be configured by using a cylindrical target as shown in FIG. 11 and irradiating electron beams to parts (denoted by reference signs 1a to 1c) of the cylindrical target. At this time, if the target is rotated, thermal influence on the target can be reduced and brighter radioactive rays can be obtained.

Since the other configurations and advantages in the fourth embodiment are similar to those of the first embodiment described above, they are not described in any further detail.

(Fifth Embodiment)

Figure 12:
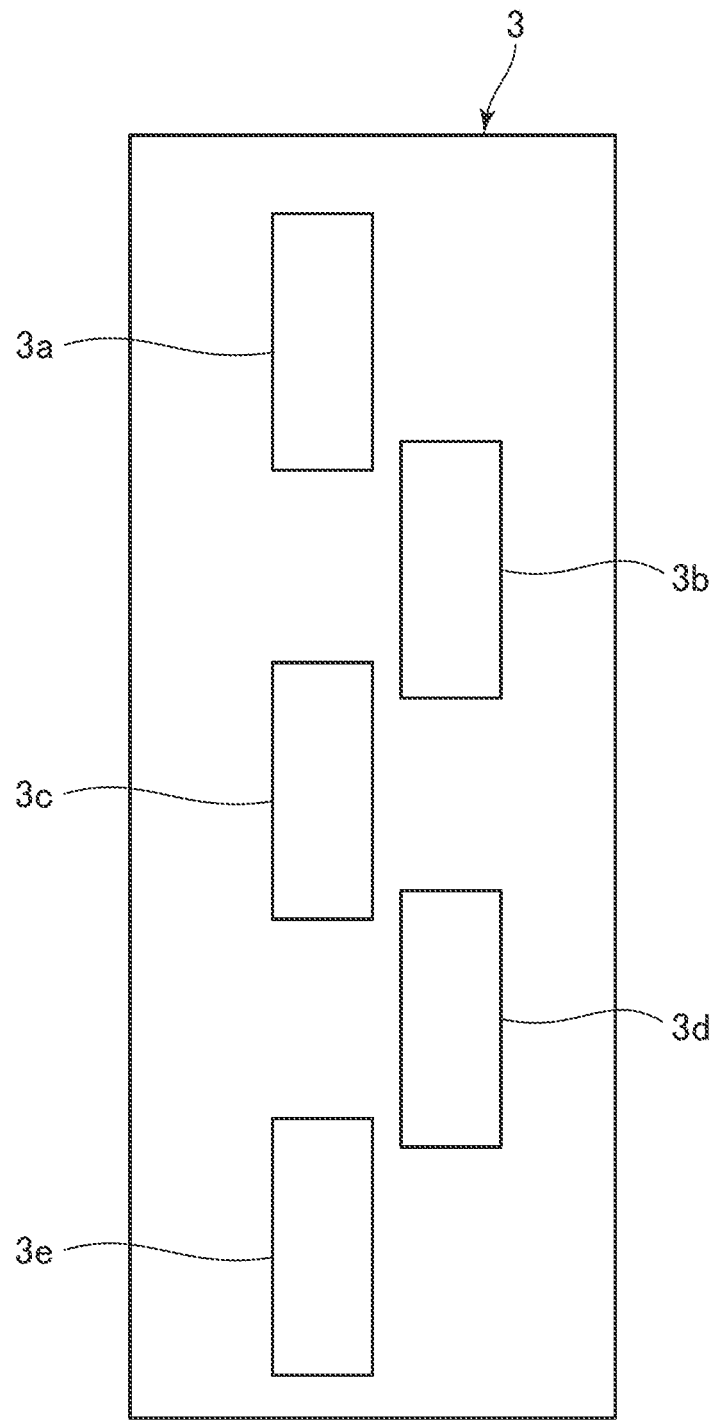
FIG. 12 is a plan view showing a configuration example of a radioactive ray detector unit in a non-destructive inspection device according to a fifth embodiment of the present invention.

Next, a non-destructive inspection device according to a fifth embodiment of the present invention is described on the basis of FIG. 12. It should be noted that elements basically common to those of the embodiments described above are denoted by the same reference signs in the description of the fifth embodiment to avoid repeated description.

Figure 13:
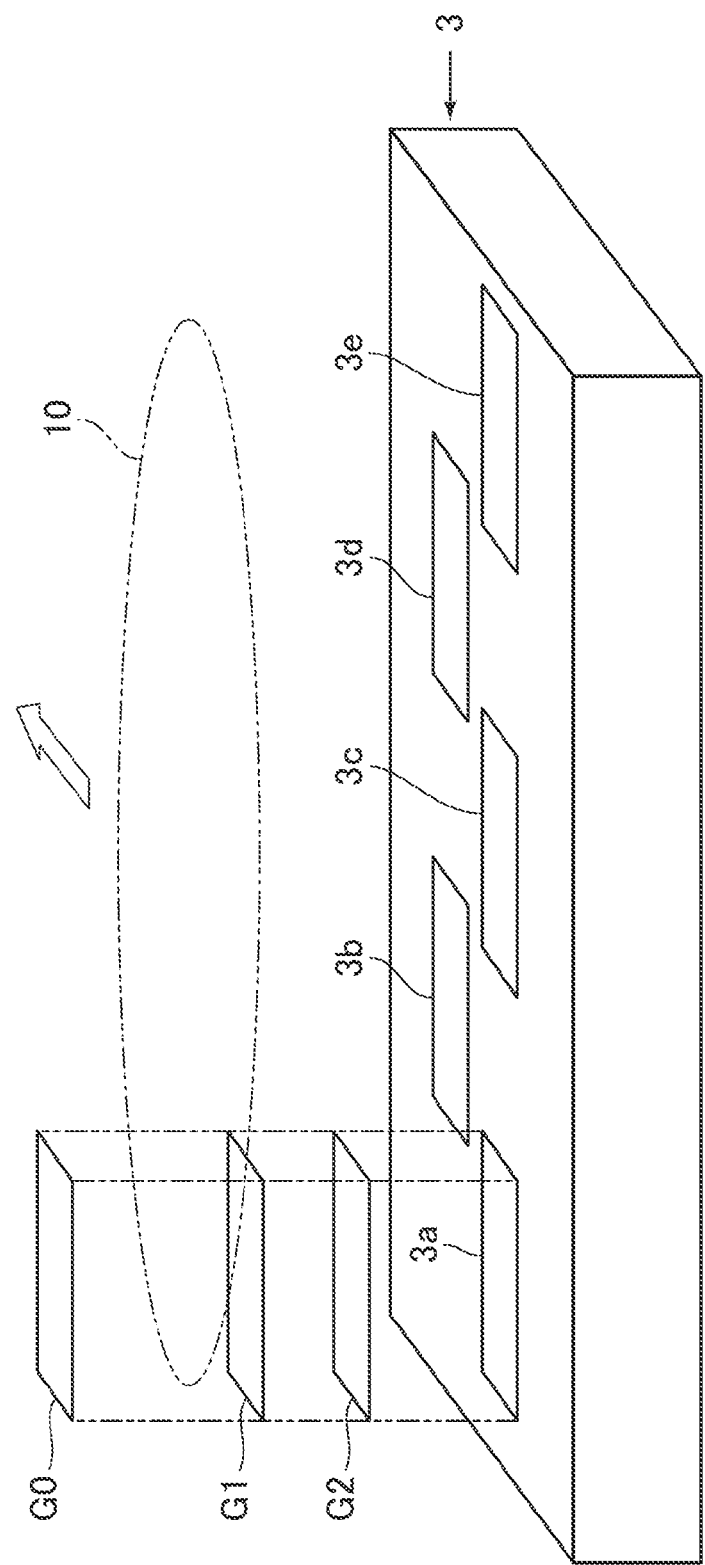
FIG. 13 is a diagram showing a positional relationship of the radioactive ray detector unit of FIG. 12 and gratings.

In the first embodiment described above, the straight line sensors are used as the radioactive ray detector unit 3. Contrary to this, in the fifth embodiment, the radioactive ray detector unit 3 is configured by arranging a plurality of sensors 3a to 3e in an offset manner. However, there is no restriction to the number of the sensors. In the present embodiment, partial gratings constituting each grating G0 to G2 are arranged above each sensor 3a to 3e as shown in FIG. 13. It should be noted that, in FIG. 13, the gratings G0 to G2 above the sensors 3b to 3e are not shown.

In the fifth embodiment, a plurality of gratings and the sensors are arranged in an offset manner and offset by a predetermined amount, but a basic configuration is similar to that of the first embodiment. However, since there are differences in the arrival time of a subject according to offset amounts (known on the side of a system) of the sensors 3a to 3e of the radioactive ray detector unit, the phase imaging method may be performed by canceling such differences in a processing unit 5.

According to the non-destructive inspection device of the fifth embodiment, there is an advantage of easily dealing with a large subject since a width of the detector unit can be easily enlarged.

Since the other configurations and advantages in the fifth embodiment are similar to those of the first embodiment described above, they are not described in any further detail.

(Sixth Embodiment)

Figure 14:
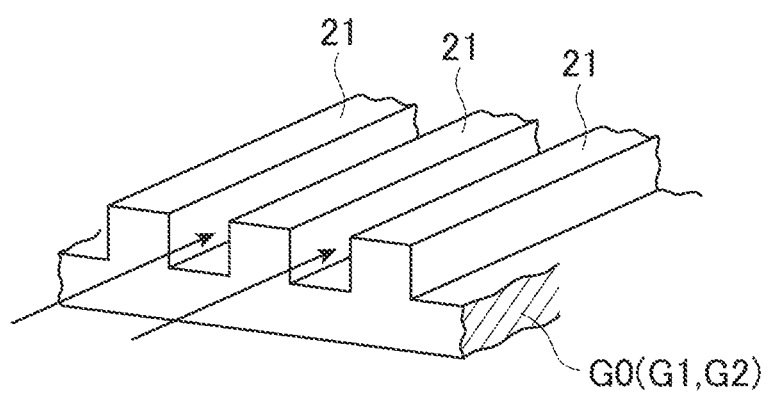
FIG. 14 is a diagram showing a configuration example of a grating in a non-destructive inspection device according to a sixth embodiment.

Next, a non-destructive inspection device according to a sixth embodiment of the present invention is described on the basis of FIG. 14. It should be noted that elements basically common to those of the embodiments described above are denoted by the same reference signs in the description of the sixth embodiment to avoid repeated description.

In the first embodiment described above, the grating members are fabricated by periodically changing a thickness of a substrate. Etching can be, for example, used as a technique for changing the thickness of the substrate. However, it is generally difficult to fabricate grating members having a high aspect ratio (width-to-thickness ratio) with high density and high accuracy.

Accordingly, in the sixth embodiment, a grating formed with unevenness in a thickness direction of a substrate is so used that radioactive rays are incident along a width of the grating (extending direction of grooves). In FIG. 14, an incident direction of radioactive rays is shown by arrows.

Since the width of the substrate can be utilized as a thickness of grating members in this way, processing is easy and a high aspect ratio can be obtained.

Since the other configurations and advantages in the sixth embodiment are similar to those of the first embodiment described above, they are not described in any further detail.

(Seventh Embodiment)

Figure 15:
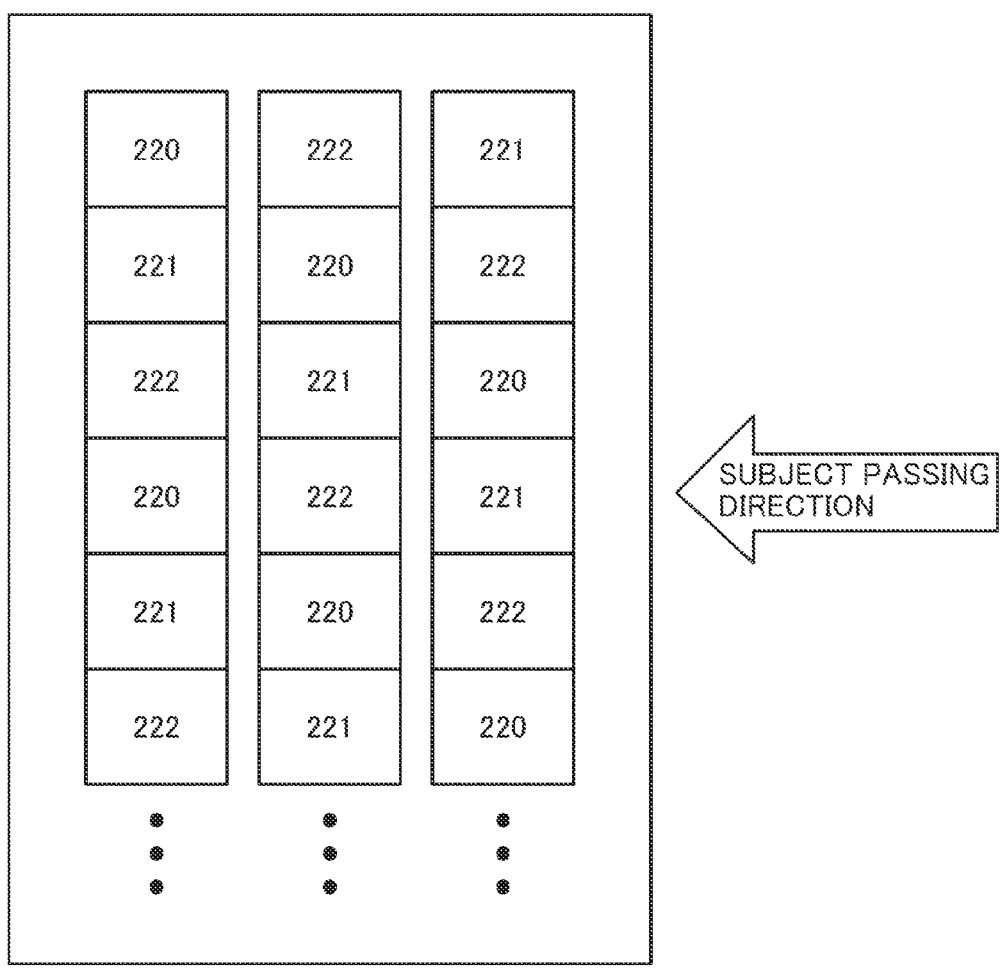
FIG. 15 is a diagram showing a configuration example of a grating in a non-destructive inspection device according to a seventh embodiment.

Next, a non-destructive inspection device according to a seventh embodiment of the present invention is described on the basis of FIG. 15. It should be noted that elements basically common to those of the embodiments described above are denoted by the same reference signs in the description of the seventh embodiment to avoid repeated description.

In the first embodiment described above, the grating members corresponding to each grating partial group 220 to 222 extend in the longer direction of the gratings (vertical direction of FIG. 3). Contrary to this, in this seventh embodiment, lengths of grating members are shortened and sets composed of three grating partial groups 220 to 222 are arranged in a longer direction of gratings (vertical direction in FIG. 15). At this time, an arrangement order can be appropriately set if a positional relationship of the three grating partial groups are known. As in the case of the first embodiment described above, the relationship of the subject position and an imaging timing can be calculated from a moving speed of a subject 10, wherefore the phase imaging method can be performed by correcting pixel positions pixel by pixel in a radioactive ray detector unit 3 in a processing unit 5.

Since the other configurations and advantages in the seventh embodiment are similar to those of the first embodiment described above, they are not described in any further detail.

(Eighth Embodiment)

Figure 16:
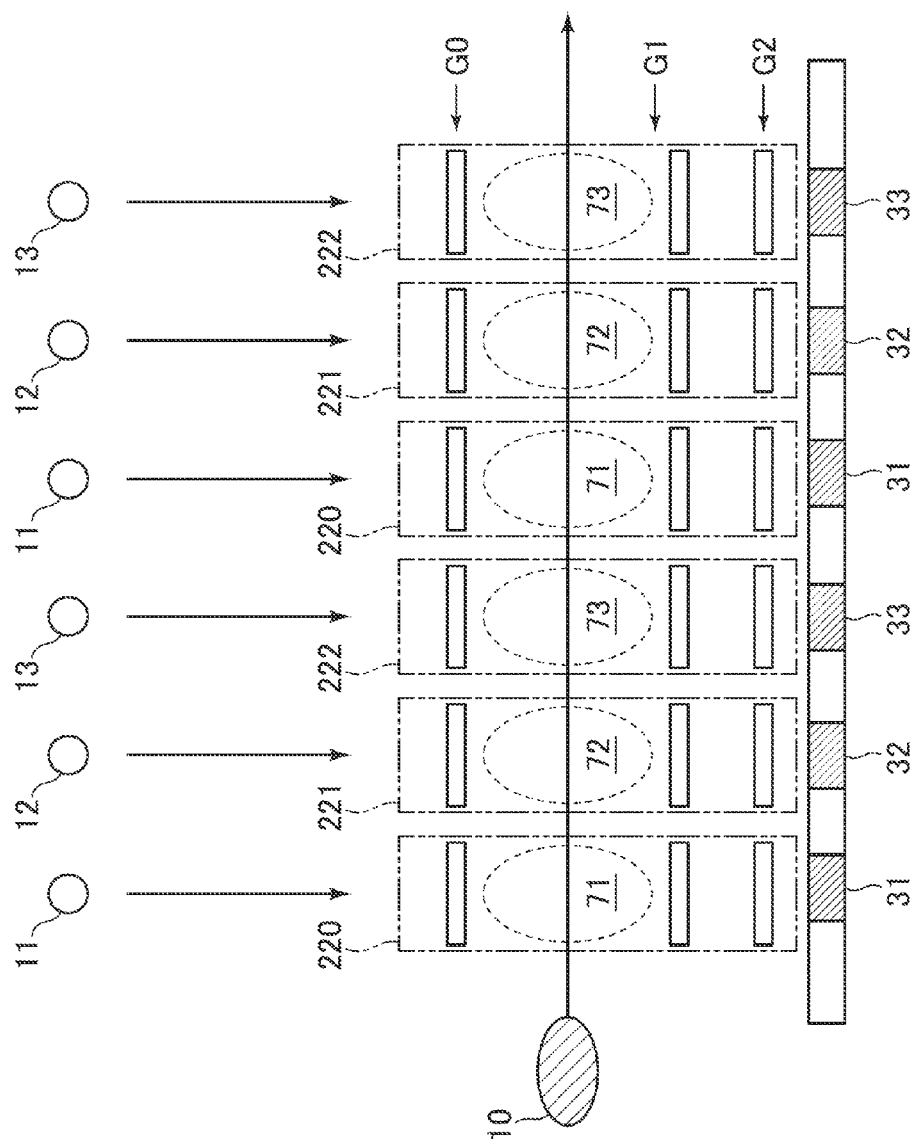
FIG. 16 is a schematic diagram of a non-destructive inspection device according to an eighth embodiment of the present invention in a plane extending along a moving direction of a subject.

Next, a non-destructive inspection device according to an eighth embodiment of the present invention is described on the basis of FIG. 16. It should be noted that elements basically common to those of the fourth embodiment described above are denoted by the same reference signs in the description of the eighth embodiment to avoid repeated description.

In this eighth embodiment, a redundant configuration is added to the configuration of the fourth embodiment. As described above, the number q of the grating partial groups including the reference grating partial group is not smaller than the division number p of the period, i.e., q≥p. Specifically, it is possible that the grating members having phase differences are present more than the necessary number p (i.e., redundant areas are present).

In an example of the eighth embodiment, the first to third partial areas 71 to 73 shown in FIG. 10 are repeatedly present along the conveying direction of the subject 10. According to this, grating partial groups 220 to 222, detectors 31 to 33, gratings G0 to G2 and first to third ray source 11 to 13 are also correspondingly repeatedly present.

By adopting such a redundant configuration, an influence on inspection accuracy due to fabrication errors of members can be alleviated.

It should be noted that a degree of redundancy to be given can be determined corresponding to conditions such as accuracy required for the device and an installation area of the device.

Since the other configurations and advantages in the eighth embodiment are similar to those of the first embodiment described above, they are not described in any further detail.

(Ninth Embodiment)

Figure 17:
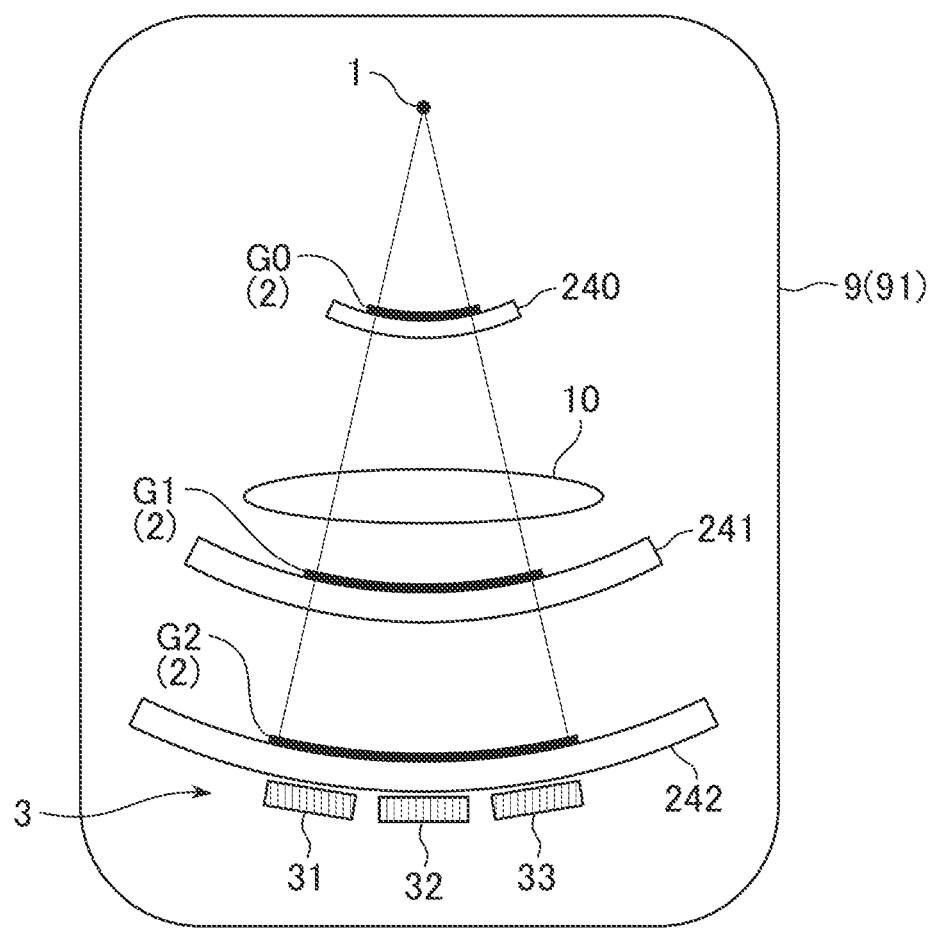
FIG. 17 is a diagram showing a schematic configuration of a driving unit in a non-destructive inspection device according to a ninth embodiment of the present invention.

Next, a non-destructive inspection device according to a ninth embodiment of the present invention is described on the basis of FIG. 17. It should be noted that elements basically common to those of the embodiments described above are denoted by the same reference signs in the description of the ninth embodiment to avoid repeated description.

The configuration of the non-destructive inspection device of this ninth embodiment is basically similar to that of the third embodiment shown in FIG. 9.

In the third embodiment shown in FIG. 9, the subject 10 is moved relative to the radiation source unit 1, the grating group 2 and the radioactive ray detector unit 3 using the conveying unit 4.

Contrary to this, in the non-destructive inspection device of the ninth embodiment, a driving unit 9 is used instead of the conveying unit 4. The driving unit 9 is configured to move a radiation source unit 1, a grating group 2 and a radioactive ray detector unit 3 as a whole relative to a subject 10 in a direction intersecting with an irradiation direction of radioactive rays.

More specifically, the driving unit 9 in the ninth embodiment is configured by a support base 91 and a driving mechanism (not shown) for rotating the support base 91 within a specified angular range centered on the position of the radiation source unit 1. The radiation source unit 1, the grating group 2 and the radioactive ray detector unit 3 are mounted on the support base 91 and rotated about the position of the radiation source unit 1 according to the rotation of the support base 91. The driving unit 9 may return the support base 91 to an initial position by rotating the support base 91 by one turn or may return the support base 91 to the initial position by rotating the support base 91 in a reverse direction.

This enables the subject 10 to relatively move with respect to the non-destructive inspection device and enables radiation image data similar to that of the third embodiment to be obtained.

It should be noted that although the radiation source unit 1 makes a rotational motion instead of a translational motion in the ninth embodiment, this case is also included in the concept of a relative "movement" with respect to the subject 10.

According to the non-destructive inspection device of the ninth embodiment, a movement of the subject 10 is not required. Thus, when the subject 10 is a living body, there is an advantage of being able to reduce burdens on the living body.

Since the other configurations and advantages in the ninth embodiment are similar to those of the third embodiment described above, they are not described in any further detail.

(Tenth Embodiment)

Figure 18:
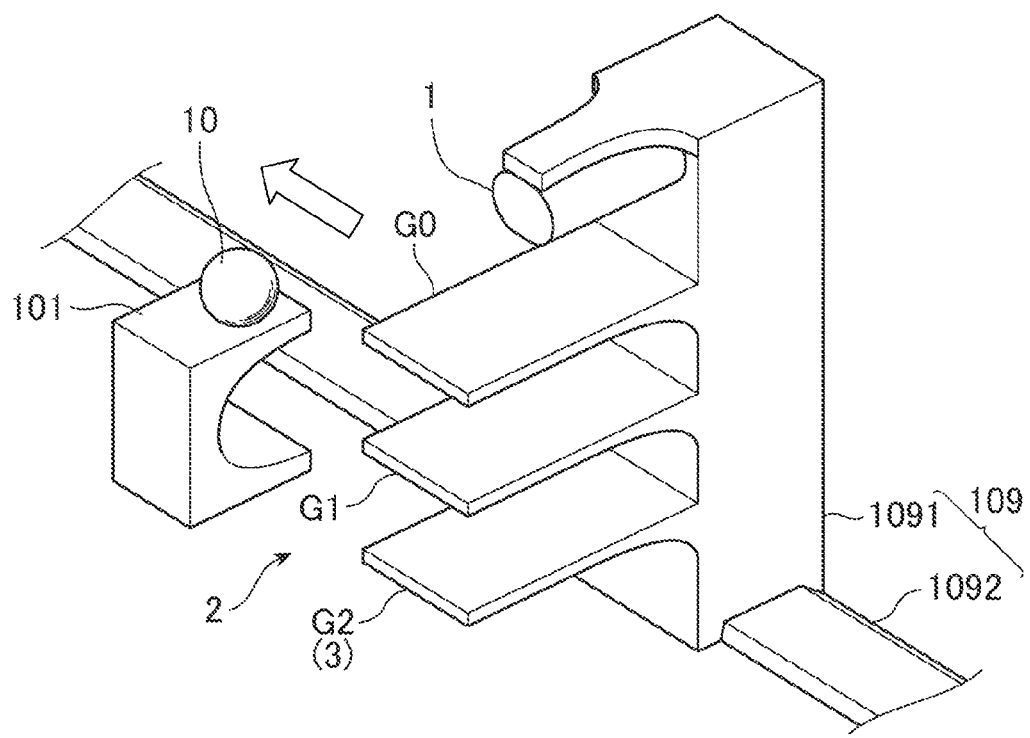
FIG. 18 is a diagram showing a schematic configuration of a driving unit in a non-destructive inspection device according to a tenth embodiment of the present invention.

Next, a non-destructive inspection device according to a tenth embodiment of the present invention is described on the basis of FIG. 18. It should be noted that elements basically common to those of the embodiments described above are denoted by the same reference signs in the description of the tenth embodiment to avoid repeated description.

The configuration of the non-destructive inspection device of this tenth embodiment is basically similar to that of the first embodiment shown in FIG. 1.

In the first embodiment shown in FIG. 1, the subject 10 is moved relative to the radiation source unit 1, the grating group 2 and the radioactive ray detector unit 3 using the conveying unit 4.

Contrary to this, in the non-destructive inspection device of the tenth embodiment, a driving unit 109 is used instead of the conveying unit 4. The driving unit 109 is configured to move a radiation source unit 1, a grating group 2 and a radioactive ray detector unit 3 as a whole relative to a subject 10 in a direction intersecting with an irradiation direction of radioactive rays.

More specifically, the driving unit 109 in the tenth embodiment includes a base unit 1091 and a rail unit 1092 for moving this base unit 1091 in a specified direction (arrow direction in FIG. 18). The radiation source unit 1, the grating group 2 and the radioactive ray detector unit 3 are mounted on the base unit 1091. The base unit 1091 is made movable along the rail unit 1092 by a specified driving mechanism (not shown).

It should be noted that, in the tenth embodiment, the radioactive ray detector unit 3 is mounted on a lower surface side of a grating G2 of the grating group 2.

Further, the subject 10 of the tenth embodiment is supported by a supporting body 101. The supporting body 101 is shaped not to obstruct the moving grating group 2 and the like. Of course, the position of the subject 10 is also set not to obstruct the moving grating group 2 and the like.

In the tenth embodiment, the subject 10 can be relatively moved with respect to the non-destructive inspection device and radiation image data similar to that of the first embodiment described above can be obtained by this configuration.

According to the non-destructive inspection device of the tenth embodiment, a movement of the subject 10 is not required. Thus, when the subject 10 is a living body, there is an advantage of being able to reduce burdens on the living body.

Since the other configurations and advantages in the tenth embodiment are similar to those of the first embodiment described above, they are not described in any further detail.

(Eleventh Embodiment)

Figure 19:
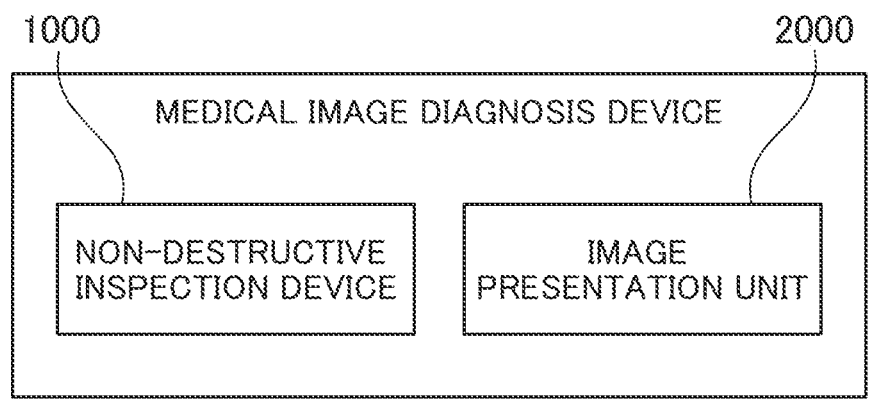
FIG. 19 is a block diagram showing a schematic configuration of a medical image diagnosis device according to an eleventh embodiment of the present invention.

Next, a medical image diagnosis device according to an eleventh embodiment of the present invention is described on the basis of FIG. 19. It should be noted that elements basically common to those of the embodiments described above are denoted by the same reference signs in the description of the eleventh embodiment to avoid repeated description.

The medical image diagnosis device of this eleventh embodiment includes a non-destructive inspection device 1000 and an image presentation unit 2000.

The non-destructive inspection device 1000 can be configured, for example, by the non-destructive inspection device of the ninth or tenth embodiment described above.

The image presentation unit 2000 is configured to present an absorption image, a refraction image or a scattering image obtained from the information of radioactive rays detected by a radioactive ray detector unit 3 as an image for diagnosis if necessary. A technique for obtaining the absorption image, the refraction image and the scattering image from the detected radioactive rays information is not described in detail since it may be similar to that described in the first embodiment.

The image presentation unit 2000 is, for example, a display for image display, but may be an output device such as a printer. In short, the image presentation unit 2000 has only to have a function of being able to present an image to a person who diagnoses (e.g., medical professional such as a doctor or a laboratory technician).

According to the medical image diagnosis device of the eleventh embodiment, an absorption image, a refraction image or a scattering image can be presented to a person, who diagnoses, if necessary when a subject 10 is a living body.

(Twelfth Embodiment)

Figure 20:
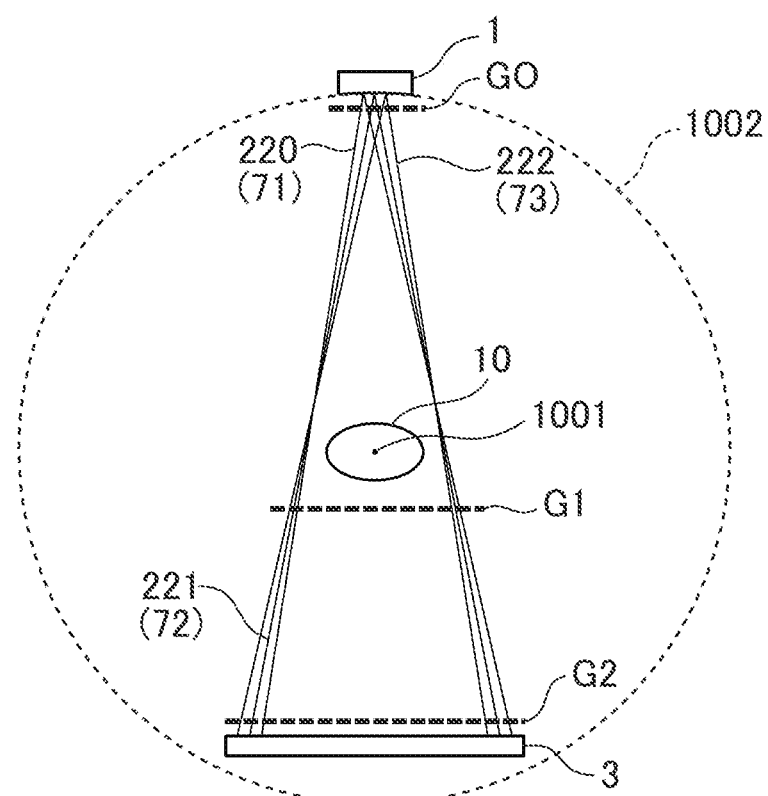
FIG. 20 is a diagram showing the configuration of a non-destructive inspection device according to a twelfth embodiment of the present invention.

Next, a non-destructive inspection device according to a twelfth embodiment of the present invention is described on the basis of FIG. 20. It should be noted that elements basically common to those of the first embodiment described above are denoted by the same reference signs in the description of the twelfth embodiment to avoid repeated description.

In the first embodiment described above, the first to third partial areas 71 to 73 are separated from each other (see FIG. 2).

Contrary to this, in this twelfth embodiment, each of first to third partial areas 71 to 73 has a part overlapping each other and non-overlapping parts (see FIG. 20). A grating member having a first phase difference (grating member constituting a first reference grating partial group 221) and a grating member having a second phase difference (grating member constituting a second reference grating partial group 222) are both arranged in the non-overlapping parts of the partial areas. Specifically, the first to third partial areas 71 to 73 in the twelfth embodiment are arranged at positions displaced little by little from each other in a direction intersecting with an irradiation direction of radioactive rays (transverse direction in FIG. 20 in this example).

Further, a radiation source unit 1 of the present embodiment is configured to irradiate radioactive rays to the first to third partial areas 71 to 73 at different timings.

More specifically, in the twelfth embodiment, a part of a grating G0 belonging to the reference grating partial group 220, a part thereof belonging to the first grating partial group 221 and a part thereof belonging to the second grating partial group 222 are arranged while being spaced apart (or adjacent) in the direction intersecting with the irradiation direction of radioactive rays. Specified phase differences (e.g., first and second phase shift sections 231, 232 in FIG. 3) are set among the part of the grating G0 belonging to the reference grating partial group 220, the part thereof belonging to the first grating partial group 221 and the part thereof belonging to the second grating partial group 222.

Further, in the non-destructive inspection device of the twelfth embodiment, the entire device can be rotated about a specified rotary shaft 1001 (see FIG. 20) in one direction or forward and reverse directions by an appropriate driving mechanism, for example, like a CT inspection device. This enables a subject 10 and the non-destructive inspection device to relatively move in the present embodiment.

In the operation of the non-destructive inspection device of the twelfth embodiment, radioactive rays are irradiated from the radiation source unit 1 to the first to third partial areas 71 to 73 at different timings. A configuration example of the radiation source unit 1 is described later. In this way, even if the first to third partial areas 71 to 73 partly overlap, the radiation image data $I_1$ to $I_3$ corresponding to each area can be separately obtained and desired subject images can be generated from those pieces of the image data. Since the phase differences are formed between the gratings in the non-overlapping parts of the first to third partial areas, the image data corresponding to these phase differences can be obtained.

Further, since the radioactive rays irradiation timings to the first to third partial areas 71 to 73 are shifted in this embodiment, the radiation image data $I_1$ to $I_3$ corresponding to each area can be obtained (specific examples are shown in Supplement 1 and 2 to be described later) even without dividing the radioactive ray detector unit 3 into a plurality of detectors.

Since the other configurations and advantages in the twelfth embodiment are similar to those of the first embodiment described above, they are not described in any further detail.

(Thirteenth Embodiment)

Figure 21:
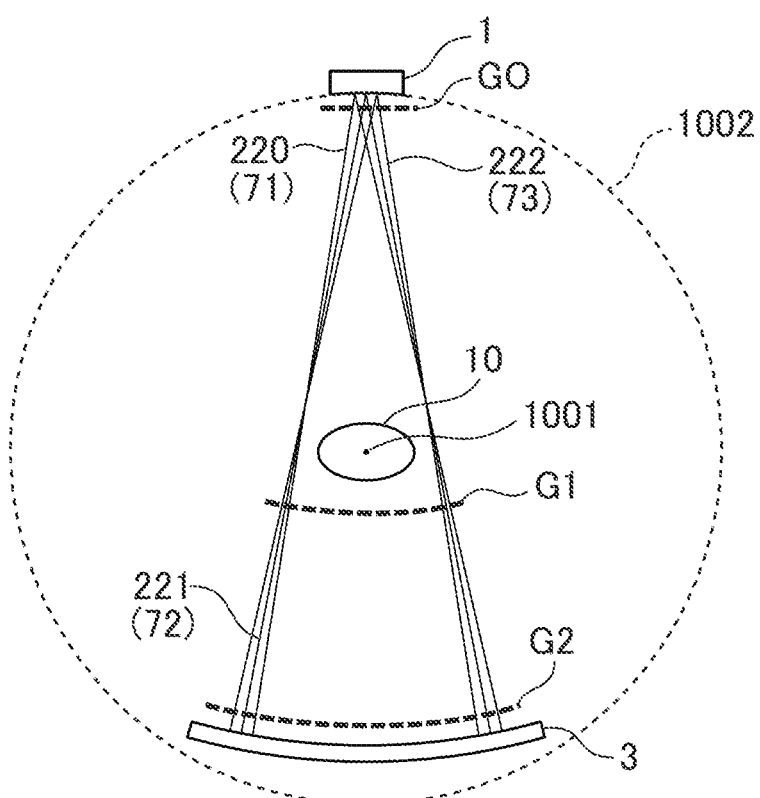
FIG. 21 is a diagram showing the configuration of a non-destructive inspection device according to a thirteenth embodiment of the present invention.

Next, a non-destructive inspection device according to a thirteenth embodiment of the present invention is described on the basis of FIG. 21. It should be noted that elements basically common to those of the twelfth embodiment described above are denoted by the same reference signs in the description of the thirteenth embodiment to avoid repeated description.

In the twelfth embodiment described above, the gratings G1 and G2 and the radioactive ray detector unit 3 are in the form of flat plates. Contrary to this, in the thirteenth embodiment, these members are arranged on concentric circles centered on a place of generating radioactive rays. This enables distances from a radiation source unit 1 to gratings G1 and G2 and a radioactive ray detector unit 3 to be kept constant. Then, there is an advantage of being able to maintain high accuracy of an obtained inspection result even when an interval of each grating is constant.

Since the other configurations and advantages in the thirteenth embodiment are similar to those of the twelfth embodiment described above, they are not described in any further detail.

(Fourteenth Embodiment)

Figure 22:
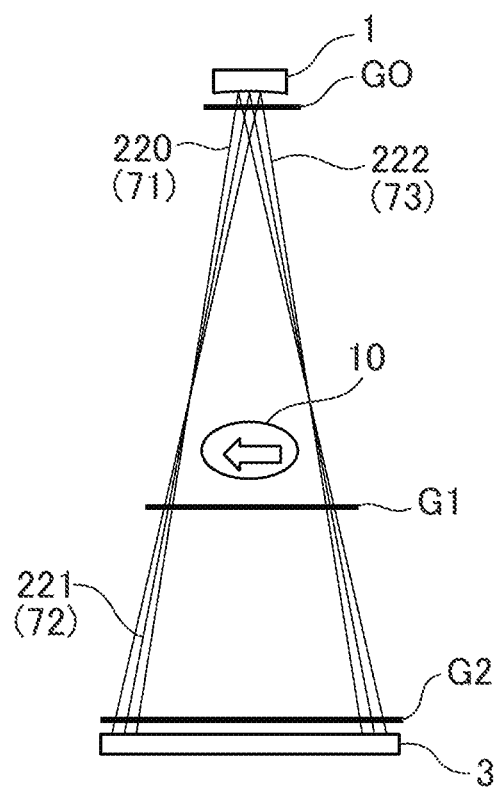
FIG. 22 is a diagram showing the configuration of a non-destructive inspection device according to a fourteenth embodiment of the present invention.

Next, a non-destructive inspection device according to a fourteenth embodiment of the present invention is described on the basis of FIG. 22. It should be noted that elements basically common to those of the twelfth embodiment described above are denoted by the same reference signs in the description of the fourteenth embodiment to avoid repeated description.

In the twelfth embodiment described above, the entire device is configured to rotate about the rotary shaft 1001. Contrary to this, in the fourteenth embodiment, the entire device is not rotated and a subject 10 is moved relative to the device, for example, by the conveying unit 4 as shown in FIG. 1. Alternatively, the subject 10 may be stationary and the device may parallelly move.

In the fourteenth embodiment, an arrangement direction (lateral direction in FIG. 22) of points (so-called foci), where radioactive rays are emitted, in a radiation source unit 1 and an extending direction of grating members in each grating (i.e., grating line) are parallel. The subject 10 moves in the lateral direction (direction parallel to the plane) in FIG. 22. It should be noted that a detailed operation in the fourteenth embodiment is described later as Supplement 3.

Since the other configurations and advantages in the fourteenth embodiment are similar to those of the twelfth embodiment described above, they are not described in any further detail.

(Fifteenth Embodiment)

Figure 23:
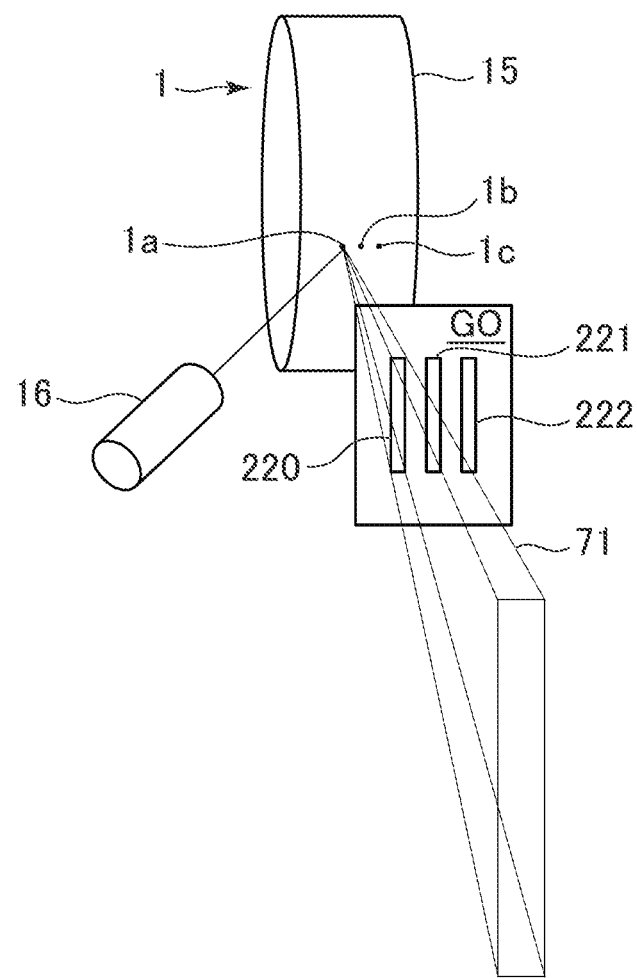
FIG. 23 is a diagram showing a radiation source unit according to a fifteenth embodiment of the present invention.

Next, a configuration example of the radiation source unit 1 useable in the non-destructive inspection devices according to the twelfth to fourteenth embodiments described above is described as a fifteenth embodiment on the basis of FIG. 23. It should be noted that elements basically common to those of the fourth embodiment described above (FIG. 11) are denoted by the same reference signs in the description of the fifteenth embodiment to avoid repeated description.

In the fifteenth embodiment, an electron beam is irradiated from an electron gun 16 to a part 1a on a cylindrical surface of a rotatable target 15. This enables radioactive rays (specifically X-rays) to be generated from the part 1a and irradiated toward a grating G0. The radioactive rays propagating from the part 1a toward a radioactive ray detector unit 3 through the grating G0 pass through a first partial area 71. Further, a part of the grating G0 where the radioactive rays generated from the part 1a pass constitutes a reference grating partial group 220 in this example. Hereinafter, similarly, a part of the grating G0 where radioactive rays generated from a part 1b pass constitutes a reference grating partial group 221 in this example and a part of the grating G0 where radioactive rays generated from a part 1c pass constitutes a reference grating partial group 222 in this example. In this example, image data obtained by the radioactive rays from the part 1a corresponds to image data $I_1$. Hereinafter, similarly, the part 1b corresponds to image data $I_2$ and the part 1c corresponds to image data $I_3$. The parts 1a to 1c described above are also called foci.

In the radiation source unit 1 of the fifteenth embodiment, the gratings G0 to G2 are arranged in a normal direction to the surface of the target 15. Then, a distance from the radioactive ray generation source to each grating is constant, wherefore there is an advantage of eliminating the need for the correction of the obtained image data $I_1$ to $I_3$.

Since the other configurations and advantages in the fifteenth embodiment are similar to those of the first embodiment described above, they are not described in any further detail.

(Sixteenth Embodiment)

Figure 24:
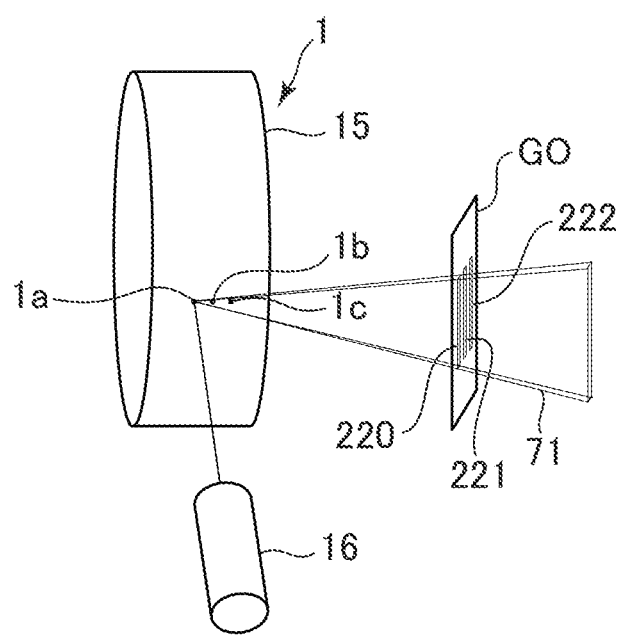
FIG. 24 is a diagram showing a radiation source unit according to a sixteenth embodiment of the present invention.

Next, a modification of the radiation source unit 1 according to the fifteenth embodiment described above is described as a sixteenth embodiment on the basis of FIG. 24. It should be noted that elements basically common to those of the fifteenth embodiment described above are denoted by the same reference signs in the description of the sixteenth embodiment to avoid repeated description.

In the sixteenth embodiment, radioactive rays are taken out in a direction inclined with respect to a cylindrical surface of a target 15 (e.g., in a direction of 6° to the surface). This configuration has an advantage of being able to increase apparent X-ray intensity. However, since a distance from a radioactive ray generation source to each grating differs in each generation place, a corresponding correction needs to be made on the obtained image data.

Since the other configurations and advantages in the sixteenth embodiment are similar to those of the fifteenth embodiment described above, they are not described in any further detail.

(Supplement 1)

Figure 25:
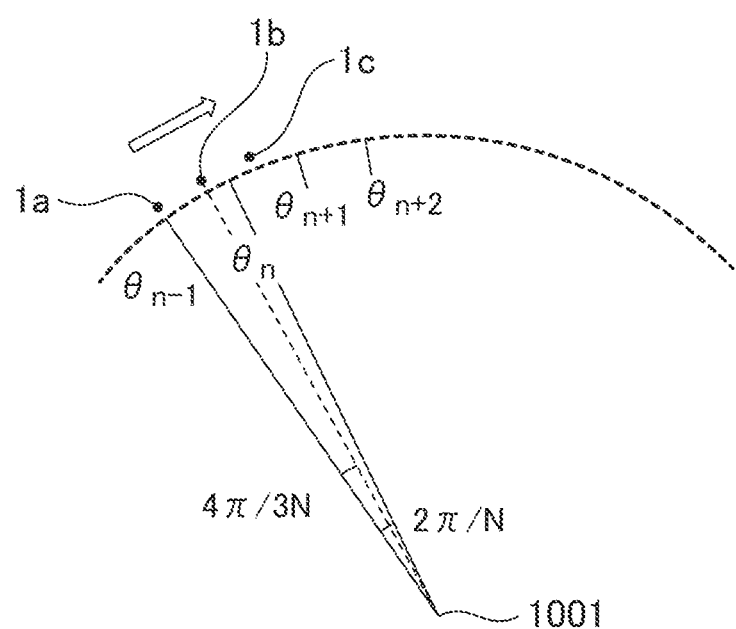
FIG. 25 is a diagram showing an example of operational expressions for a radioactive rays projection image obtained in the twelfth and thirteenth embodiments.
Figure 26:
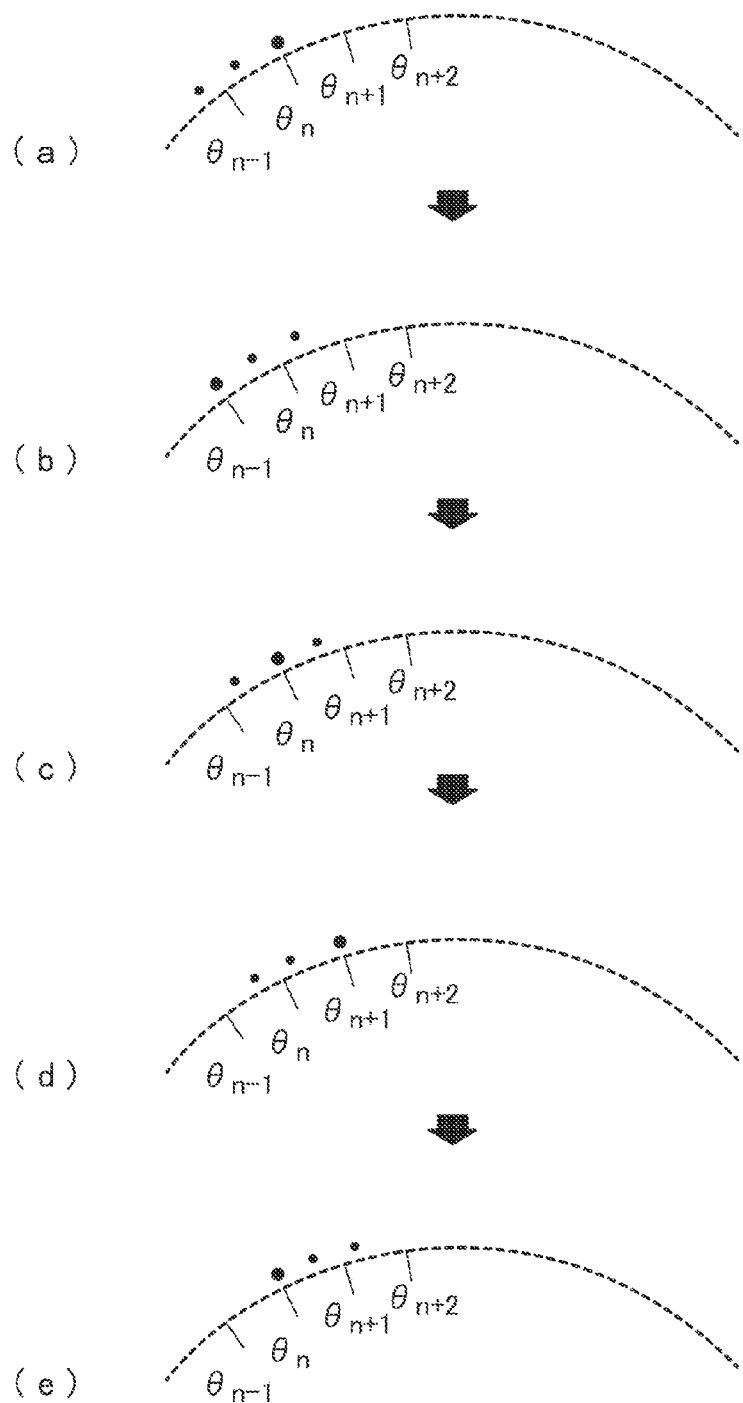
FIGS. 26(a) to 26(e) are diagrams showing the example of the operational expressions for the radioactive rays projection image obtained in the twelfth and thirteenth embodiments.

An example of operational expressions for radioactive rays projection images obtained in the twelfth and thirteenth embodiments described above is described below further with reference to FIGS. 25 and 26.

Operational expressions for projection images (absorption image $T_n$, refraction image $D_n$ and scattering image $V_n$) when X-rays are irradiated to the subject 10 (see FIGS. 20 and 21) in a direction of $\theta_n$ about the rotary shaft 1001 are described below. Here, n=1, 2, ..., N and projection images obtained by equally dividing 360° ($2\pi$) by N are obtained and used for CT image reconstruction.

It is assumed that an angle difference of each focus is $4\pi/(3N)$ when viewed from a rotation center 1001. It should be noted that although three foci are assumed here, an argument similar to the following one holds even if the number of the foci increases. An order of blinking (presence and absence of X-ray generation by electron beam irradiation) of each focus can be set as in FIGS. 26(a) to 26(e). Here, a large black dot indicates the focus where X-rays are generated at that point of time. Three images $I_n^k(x, y)$ (k=1, 2, 3) by the blinking of each focus can be obtained in a projection direction $\theta_n$. As can be understood from FIG. 26, these are not necessarily images continuously recorded in time series. However, since each projection direction is known, a rearrangement can be made in a computer after a measurement in correspondence with the projection direction. Since $I_n^k(x, y)$ (k=1, 2, 3) are images from different foci, images of a subject on the detector are shifted from each other by a predetermined angle. That shift amount when a distance from the rotation center 1001 to the detector is $R_2$ is:

$$\frac{4\pi}{3N}R_2.$$

Accordingly, if an x-axis is selected in a shift direction, the absorption image $T_n$, the refraction image $D_n$ and the scattering image $V_n$ can be calculated as follows.

$$T_n(x, y) = \frac{I_n^1(x, y) + I_n^2(x - 4\pi R_2/3N, y) + I_n^3(x - 8\pi N_2/3N, y)}{\hat{I}_n^1(x, y) + \hat{I}_n^2(x - 4\pi R_2/3N, y) + \hat{I}_n^3(x - 8\pi R_2/3N, y)}$$

-continued $$D_n(x, y) = \arg\left[\frac{S_n(x, y)}{\hat{S}_n(x, y)}\right]$$

where $S_n(x, y) =$ $$I_n^1(x, y) + I_n^2(x - 4\pi R_2/3N, y)\exp\left(\frac{2}{3}\pi i\right) + I_n^3(x - 8\pi R_2/3N, y)\exp\left(\frac{4}{3}\pi i\right)$$

$$\hat{S}_n(x, y) = \hat{I}_n^1(x, y) + \hat{I}_n^2(x - 4\pi R_2/3N, y)\exp\left(\frac{2}{3}\pi i\right) +$$

$$\hat{I}_n^3(x - 8\pi R_2/3N, y)\exp\left(\frac{4}{3}\pi i\right)$$

and $$V_n(x, y) = \frac{S_n(x, y)}{\hat{S}_n(x, y)T(x, y)}$$

It should be noted that a symbol hat (^) indicates an image measured in the absence of the subject.

(Supplement 2)

Figure 27:
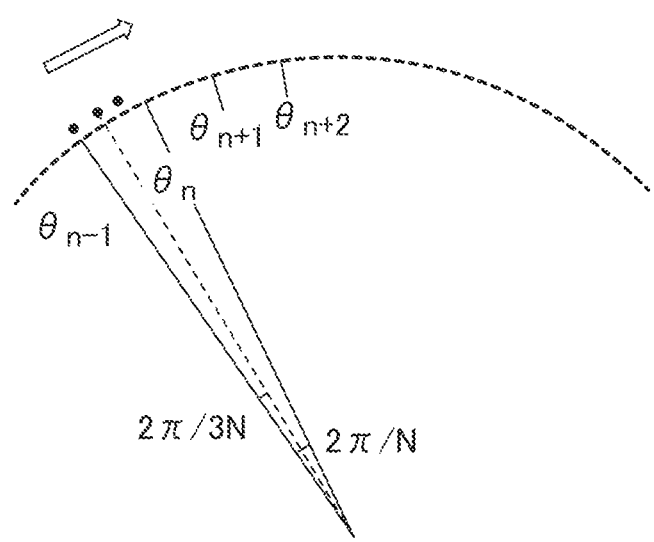
FIG. 27 is a diagram showing another example of the operational expressions for the radioactive rays projection image obtained in the twelfth and thirteenth embodiments.
Figure 28:
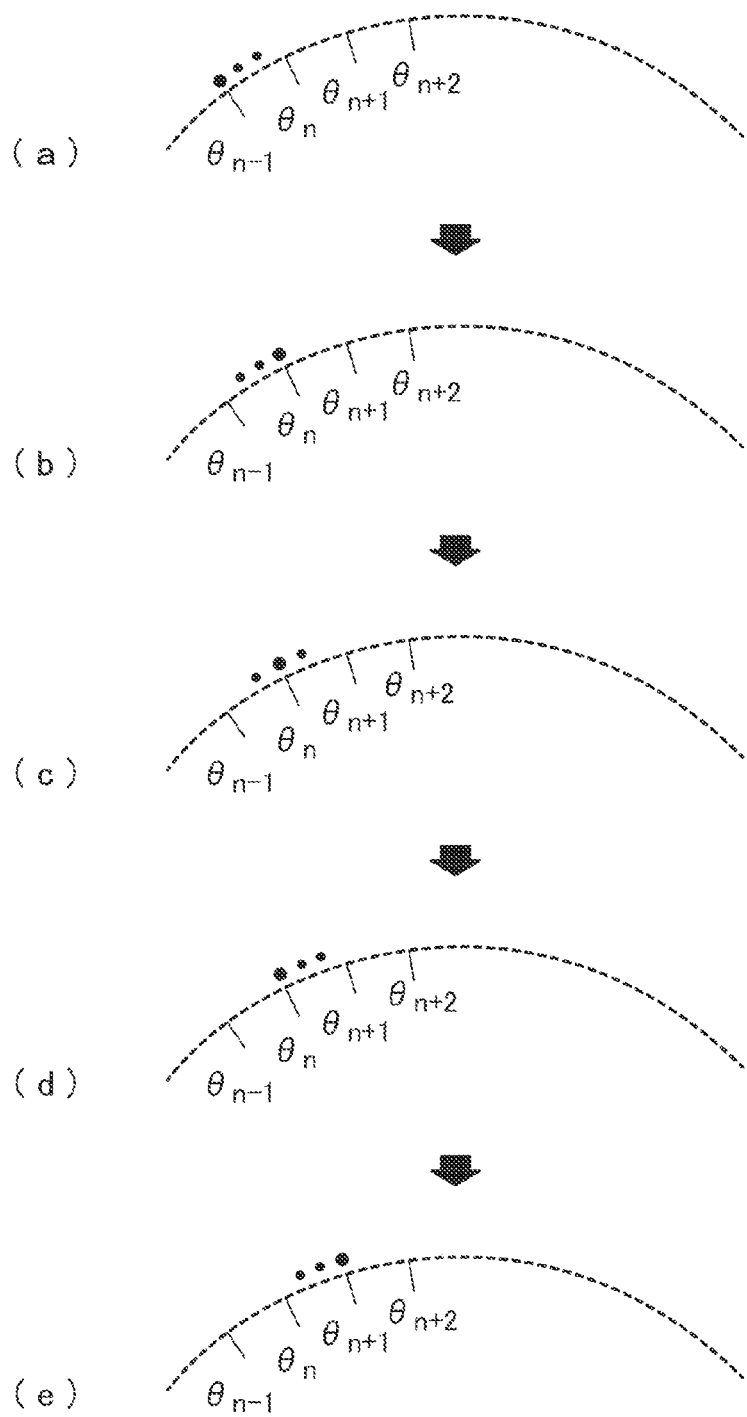
FIGS. 28(a) to 28(e) are diagrams showing the other example of the operational expressions for the radioactive rays projection image obtained in the twelfth and thirteenth embodiments.

Another example of operational expressions for radioactive rays projection images obtained in the twelfth and thirteenth embodiments described above are shown below. It is assumed that an angle difference of each focus is $2\pi/(3N)$ when viewed from the rotation shaft 1001 (see FIG. 27). It should be noted that although three foci are assumed here, an argument similar to the following one holds even if the number of the foci increases. An order of blinking of each focus can be set as in FIG. 28 and three images $I_n^k(x, y)$ (k=1, 2, 3) by the blinking of each focus can be obtained in the projection direction $\theta_n$. A calculation method for the absorption image $T_n$, the refraction image $D_n$ and the scattering image $V_n$ is the same as in the case of Supplement 1 described above.

It should be noted that the description of Supplement 1 and 2 described above more precisely matches in the thirteenth embodiment using the curved detector (FIG. 21). The above description can be approximately applied in the twelfth embodiment (FIG. 20).

(Supplement 3)

An example of operational expressions for radioactive rays projection images obtained in the fourteenth embodiment described above is described below. It is assumed that 'a' denotes a distance between foci and $\Delta t$ denotes a time interval of successively blinking each focus. Further, it is assumed that v denotes a speed of the subject and the blinking of the foci and the motion of the subject are synchronized if $v=a/\Delta t$ is satisfied. If n denotes the number of cycles of blinking all three foci, three images $I_n^k(x, y)$ (k=1, 2, 3) corresponding to the blinking of each focus are recorded on the image detector (i.e., radioactive ray detector unit 3) in the $n^{th}$ cycle. If a moving direction of the subject is represented by +x, the absorption image $T_n$, refraction image $D_n$ and scattering image $V_n$ of the cycle n can be calculated by:

$$T_n(x, y) = \frac{I_n^1(x, y) + I_n^2(x+a, y) + I_n^3(x+2a, y)}{\hat{I}_n^1(x, y) + \hat{I}_n^2(x+a, y) + \hat{I}_n^3(x+2a, y)}$$

$$D_n(x, y) = \arg\left[\frac{S_n(x, y)}{\hat{S}_n(x, y)}\right]$$

where $$S_n(x, y) = I_n^1(x, y) + I_n^2(x+a, y)\exp\left(\frac{2}{3}\pi i\right) + I_n^3(x+2a, y)\exp\left(\frac{4}{3}\pi i\right)$$

$$\hat{S}_n(x, y) = \hat{I}_n^1(x, y) + \hat{I}_n^2(x+a, y)\exp\left(\frac{2}{3}\pi i\right) + \hat{I}_n^3(x+2a, y)\exp\left(\frac{4}{3}\pi i\right)$$

and $$V_n(x, y) = \frac{S_n(x, y)}{\hat{S}_n(x, y)T(x, y)}$$

It should be noted that a symbol hat (^) indicates an image measured in the absence of the subject.

To improve S/N of a final image, images of each cycle can be added as follows.

$$T(x, y) = \sum_n T_n(x + 3na)$$

$$D(x, y) = \sum_n D_n(x + 3na)$$

$$V(x, y) = \sum_n V_n(x + 3na)$$

It should be noted that the above embodiments and examples are merely examples and do not indicate configurations essential for the present invention. The configuration of each part is not limited to the above if the gist of the present invention can be achieved.

For example, although the X-ray source is used as the radiation source in each of the above embodiments, other radioactive rays having transmissivity to a subject, e.g., a neutron ray source can be used. Of course, in this case, a detector capable of detecting used radioactive rays is used as the radioactive ray detector.

Further, as already described, the number of the gratings constituting the grating group may be two by omitting the grating G0 or G2.

LIST OF REFERENCE SIGNS

1 radiation source unit
11 to 13 first to third ray source
2 grating group
G0 to G2 gratings
21 grating member
220 reference grating partial group
221 to 222 first and second grating partial groups
231 to 232 first and second phase shift sections
240 to 242 G0 to G2 holders
3 radioactive ray detector unit
31 to 33 detector
4 conveying unit
5 processing unit
6 control unit
7 radioactive ray passage area
71 to 73 first to third partial areas
8 output unit
9, 109 driving unit
91 support base
1091 base unit
1092 rail unit
10 subject
101 supporting body
1000 non-destructive inspection device
2000 image presentation unit

The invention claimed is:

1. A non-destructive inspection device, comprising a radiation source unit, a grating group and a radiation ray detector unit, wherein:
the radiation source unit is configured to irradiate radiation rays having transmissivity to a subject toward the grating group;
the grating group is composed of a plurality of gratings that transmit the radiation rays irradiated toward the grating group;
each of the plurality of gratings includes a plurality of grating members arranged at a predetermined period determined for each grating;
the radiation ray detector unit is configured to detect the radiation rays diffracted by the plurality of grating members;
a radiation ray passage area through which the radiation rays irradiated from the radiation source unit and reaching the radiation ray detector unit pass includes at least first to third partial areas;
the first to third partial areas are arranged at positions displaced from each other in a direction intersecting with an irradiation direction of the radiation rays; and
when a part of the grating group located in a space through which each of the radiation rays to be transmitted through any one of the first to third partial areas passes is called a reference grating partial group and parts of the grating group located in spaces through which the radiation rays to be transmitted through the other ones of the first to third partial areas pass are respectively called first and second grating partial groups, the grating members of some of the gratings included in the reference grating partial group are arranged at the predetermined period in this grating, some of the gratings included in the first grating partial group includes a grating member having a first phase difference with respect to the arrangement at the predetermined period in some of these gratings, and some of the gratings included in the second grating partial group includes a grating member having a second phase difference with respect to the arrangement at the predetermined period in some of these gratings, wherein:
each of the first to third partial areas includes a mutually overlapping part and a non-overlapping part;
the grating member having the first phase difference and the grating member having the second phase difference are both arranged in the non-overlapping parts; and
the radiation source unit is configured to irradiate the radiation rays to the first to third partial areas at different timings; and
wherein:
one of the plurality of gratings is a G0 grating which constitutes a micro radiation source array,
a part of the G0 grating belonging to the reference grating partial group, a part of the G0 grating belonging to the first grating partial group, and a part of the G0 grating belonging to the second grating partial group are arranged while being spaced apart or adjacent in the direction intersecting with the irradiation direction of the radiation rays, and
the first and second phase differences are set between the part of the G0 grating belonging to the reference grating partial group, the part thereof belonging to the first grating partial group, and the part thereof belonging to the second grating partial group.

2. The non-destructive inspection device according to claim 1, wherein:
the radiation ray detector unit is configured to detect the radiation rays transmitted through the reference grating partial group, the radiation rays transmitted through the first grating partial group and the radiation rays transmitted through the second grating partial group.

3. The non-destructive inspection device according to claim 2, further comprising a processing unit, wherein:
the processing unit is configured to calculate any one of an absorption image, a refraction image and a scattering image of the subject using detection values of the radiation rays transmitted through the reference grating partial group, detection values of the radiation rays transmitted through the first grating partial group and detection values of the radiation rays transmitted through the second grating partial group.

4. The non-destructive inspection device according to claim 1, further comprising a conveying unit, wherein:
the conveying unit is configured to move the subject relative to the grating group in the direction interesting with the irradiation direction of the radiation rays.

5. The non-destructive inspection device according to claim 1, wherein:
the grating group is composed of two gratings.

6. The non-destructive inspection device according to claim 1, wherein:
the grating group is composed of three gratings.

7. The non-destructive inspection device according to claim 1, wherein:
the radiation source unit includes first to third ray sources;
the first ray source unit is configured to irradiate the radiation rays transmitted through the first partial area;
the second ray source unit is configured to irradiate the radiation rays transmitted through the second partial area; and
the third ray source unit is configured to irradiate the radiation rays transmitted through the third partial area.

8. The non-destructive inspection device according to claim 1, wherein:
the first and second phase differences are set at values capable of performing phase imaging using a detection result of the radiation rays transmitted through the reference grating partial group, a detection result of the radiation rays transmitted through the first grating partial group and a detection result of the radiation rays transmitted through the second grating partial group.

9. The non-destructive inspection device according to claim 1, wherein:
the radiation rays are X-rays or neutron rays.

10. The non-destructive inspection device according to claim 1, further comprising a driving unit, wherein:
the driving unit is configured to move the radiation source unit, the grating group and the radiation ray detector unit as a whole relative to the subject in the direction intersecting with the irradiation direction of the radiation rays.

11. The non-destructive inspection device according to claim 1, wherein:
the subject is a living body.

12. A medical image diagnosis device, comprising the non-destructive inspection device according to claim 11 and an image presentation unit, wherein:
the image presentation unit is configured to present an absorption image, a refraction image or a scattering image obtained from information of the radiation rays detected by the radiation ray detector unit as an image for diagnosis.

13. A non-destructive inspection method using the non-destructive inspection device according to claim 1, comprising:
- a step of moving the subject relative to the grating group in the direction intersecting with the irradiation direction of the radiation rays;
- a step of detecting the radiation rays transmitted through the subject when the subject passes through the reference grating partial group;
- a step of detecting the radiation rays transmitted through the subject when the subject passes through the first grating partial group; and
- a step of detecting the radiation rays transmitted through the subject when the subject passes through the second grating partial group.

14. The non-destructive inspection device according to claim 1, wherein:
- the entire non-destructive inspection device rotatable about a rotation axis that passes through the subject so that the subject moves relative to the non-destructive inspection device.

* * * * *